US012636285B2

(12) United States Patent
Crauwels et al.

(10) Patent No.: US 12,636,285 B2
(45) Date of Patent: May 26, 2026

(54) METHOD FOR TREATING HIV WITH CABOTEGRAVIR AND RILPIVIRINE

(71) Applicants: ViiV Healthcare Company, Wilmington, DE (US); Janssen Sciences Ireland Unlimited Company, Ringaskiddy (IE)

(72) Inventors: Herta Maria Ludovica Crauwels, Beerse (BE); Susan L. Ford, Research Triangle Park, NC (US); David Andrew Margolis, Research Triangle Park, NC (US); Stefaan Louis F. Rossenu, Beerse (BE); William Robert Spreen, Research Triangle Park, NC (US); Rodica Mihaela Van Solingen-Ristea, Beerse (BE); Peter Evan Owen Williams, Buckinghamshire (GB)

(73) Assignees: ViiV Healthcare Company, Wilmington, DE (US); Janssen Sciences Ireland Unlimited Company, Ringaskiddy (IE)

(*) Notice: Subject to any disclaimer, the term of this patent is extended or adjusted under 35 U.S.C. 154(b) by 0 days.

(21) Appl. No.: 19/227,593

(22) Filed: Jun. 4, 2025

(65) Prior Publication Data

US 2025/0302829 A1 Oct. 2, 2025

Related U.S. Application Data

(63) Continuation of application No. 17/763,076, filed as application No. PCT/IB2020/059185 on Oct. 1, 2020.

(60) Provisional application No. 63/052,214, filed on Jul. 15, 2020, provisional application No. 63/037,782, filed on Jun. 11, 2020, provisional application No. 62/908,995, filed on Oct. 1, 2019, provisional application No. 62/908,882, filed on Oct. 1, 2019.

(51) Int. Cl.

| | |
|---|---|
| ***A61K 31/4985*** | (2006.01) |
| ***A61K 9/00*** | (2006.01) |
| ***A61K 9/20*** | (2006.01) |
| ***A61K 31/505*** | (2006.01) |
| ***A61P 31/18*** | (2006.01) |

(52) U.S. Cl.

CPC ........ *A61K 31/4985* (2013.01); *A61K 9/0019* (2013.01); *A61K 9/0053* (2013.01); *A61K 9/20* (2013.01); *A61K 31/505* (2013.01); *A61P 31/18* (2018.01)

(58) Field of Classification Search

CPC .................................................. A61K 31/4985

See application file for complete search history.

(56) References Cited

U.S. PATENT DOCUMENTS

| | | | | |
|---|---|---|---|---|
| 11,564,921 | B2 * | 1/2023 | Crauwels | A61K 31/4985 |
| 12,178,815 | B2 * | 12/2024 | Crauwels | A61P 31/18 |
| 2002/0198388 | A1 | 12/2002 | Hale et al. | |
| 2003/0207871 | A1 | 11/2003 | Tung et al. | |
| 2004/0122000 | A1 | 6/2004 | Hale et al. | |
| 2015/0313917 | A1 | 11/2015 | Cai et al. | |
| 2017/0246118 | A1 | 8/2017 | Johns | |
| 2020/0147079 | A1 * | 5/2020 | Crauwels | A61P 31/18 |
| 2021/0323967 | A1 * | 10/2021 | Gillis | A61K 9/0019 |

FOREIGN PATENT DOCUMENTS

| | | | |
|---|---|---|---|
| CN | 102573815 | A | 7/2012 |
| CN | 109568328 | A | 4/2019 |
| WO | 2007147882 | A2 | 12/2007 |
| WO | 2011036159 | A2 | 3/2011 |
| WO | 2011094150 | A1 | 8/2011 |
| WO | 2016036759 | A1 | 3/2016 |
| WO | 2016046786 | A1 | 3/2016 |
| WO | 2019016732 | A1 | 1/2019 |

OTHER PUBLICATIONS

Clinical Trials: NCT02951052: A Phase III, Randomized, Multi-center, Parallel-group, Noninferiority, Open-label Study Evaluating the Efficacy, Safety, and Tolerability of Switching to Long-acting Cabotegravir plus Longacting Rilpivirine from Current Ini- Nnrti-, or Pi-based Antiretroviral Regimen in Hiv-1-infected Adults Who Are Virologically Suppressed,[online], Jan. 2019 URL:https://cdn.clinicaltrials.gov/large-docs/52/NCT02951052/Prot_000.pdf.

ClinicalTrials: NCT02951052: Study Evaluating the Efficacy, Safety, and Tolerability of Switching to Long-acting Cabotegravir Plus Long-acting Rilpivirine From Current Antiretroviral Regimen in Virologically Suppressed HIV-1-infected Adults,[online], Jul. 2019 URL:https://clinicaltrials.gov/study/NCT02951052term=NCT02951052&rank=1&tab=history&a=52.

Fernandez C. et al., "Evaluating Cabotegravir/rilpivirine Long-acting, Injectable in the Treatment of Hiv Infection: Emerging Data and Therapeutic Potential", HIV/AIDS—Research and Palliative Care, 2019, vol. 11, pp. 179-192.

Han K., et al., "1532. Population Pharmacokinetic (PPK) Modeling and Simulation of Long-acting (LA) Cabotegravir (CAB) to Inform Strategies Following Dosing Interruptions in HIV-1-infected Subjects-PMC (nih.gov)," Oct. 4, 2019, 1 Page.

International Preliminary Report on Patentability for International Application No. PCT/IB2020/059185 , mailed Apr. 14, 2022, 11 Pages.

International Search Report and Written Opinion for International Application No. PCT/IB2020/059185, mailed Dec. 14, 2020, 13 Pages.

"Long-term Safety and Efficacy of CAB and RPV as 2-Drug Oral Maintenance Therapy," 2019 URL: https://www.croiconference.org/wp-content/uploads/sites/2/posters/2017/442_Margolis.pdf.

(Continued)

*Primary Examiner* — Rei Tsang Shiao

(74) *Attorney, Agent, or Firm* — William B. Stauffer

(57) ABSTRACT

Invented are methods for treating HIV in a human in need thereof which comprises the administration of a therapeutically effective amount of a combination of cabotegravir or a pharmaceutically acceptable salt thereof and rilpivirine or a pharmaceutically acceptable salt thereof, to such human.

24 Claims, 1 Drawing Sheet

(56) References Cited

OTHER PUBLICATIONS

Margolis D.A., et al., "Cabotegravir Plus Rilpivirine, Once a Day, After Induction With Cabotegravir Plus Nucleoside Reverse Transcriptase Inhibitors in Antiretroviral-Naive Adults With HIV-1 infection (LATTE): a Randomised, Phase 2b, Dose-Ranging Trial," The Lancet Infectious Diseases, Oct. 1, 2015, vol. 15, No. 10, ISSN 1474-4457, pp. 1145-1155, Aug. 2013, XP002802307.
Margolis D.A., et al., "Long-Acting Intramuscular Cabotegravir and Rilpivirine in Adults With HIV-1 Infection (LATTE-2): 96-Week Results of a Randomised, Open-Label, Phase 2b, Non-inferiority Trial," Lancet, 2017, vol. 390, No. 10101, pp. 1499-1510.
Orkin, C., et al., "Long-Acting Cabotegravir and Rilpivirine after Oral Induction for HIV-1 Infection," The New England Journal of Medicine, Mar. 19, 2020, vol. 382(12), pp. 1124-1135.
Orkin C., et al., "Long-Acting Cabotegravir+Rilpivirine for HIV Maintenance: Flair Week 48 Results," 25th Annual Conference of the British HIV Association, Bhiva, Mar. 7, 2019, DOI: ttps://www.natap.org/2019/CROI/croi_65.htm. XP055756158.
Orkin, C., et al., "Long-active cabotegravir + rilpivirine for HIV Maintenance: FLAIR week-48 Results," Oral Abstracts 010, HIV Medicine, Apr. 2019, vol. 20 (Suppl. 5), pp. 3-15.
Orkin C., et al., "Oral Abstracts Oral Research Presentations Session 1 01 the Impact of the Introduction of a Specialist HIV Pharmacy Service (SHPS) to Satellite HIV Clinics," HIV Medicine, Apr. 1, 2019, vol. 20, pp. 3-15, XP055756333, DOI: https://onlinelibrary.wiley.com/doi/full/10.1111/hiv.12738, p. 6-p. 7.
Shaik J.S.B., et al., "A Phase 1 Study to Evaluate the Pharmacokinetics and Safety of Cabotegravir in Patients With Hepatic Impairment and Healthy Matched Controls," Clinical Harmacology in Drug Development, Feb. 27, 2019, vol. 8, No. 5, pp. 664-673, col. 1. DOI: 10.1002/cpdd.655, ISSN: 2160-763X, XP055756348.
Spreen W.R., et al., "Long-acting Injectable Antiretrovirals for Hiv Treatment and Prevention" Current Opinion, 2013, vol. 8(6), pp. 565 to 571.
Teichner, P. et al., "Patient Adherence to Long-Acting Injectable Cabotegravir + Rilpivirine Through 48 Weeks of Maintenance Therapy in the Phase 3 ATLAS and FLAIR Studies," Oral Abstracts 884, Open Forum Infectious Diseases, Oct. 23, 2019, Retrieved from the internet: https://academic.oup.com/ofid/article/6/Supplement_2/520/5604664 (retrieved Nov. 15, 2024), p. 1, col. 1 q.
Clinical Trials.gov Identifier: NCT02938520: Study to Evaluate the Efficacy, Safety, and Tolerability of Long-acting Intramuscular Cabotegravir and Rilpivirine for Maintenance of Virologic Suppression Following Switch From an Integrase Inhibitor in HIV-1 Infected Therapy Naive Participants, https://clinicaltrials.gov/study/NCT02938520. 15, 2024, 14 Pages, Available at https://clinicaltrials.gov/study/NCT02938520?tab=history&a=39#version-content-panel February.
Clinical Trials.gov Identifier: NCT02951052: Study Evaluating the Efficacy, Safety, and Tolerability of Switching to Long-acting Cabotegravir Plus Long-acting Rilpivirine From Current Antiretroviral Regimen in Virologically Suppressed HIV-1-infected Adults. https://clinicaltrials.gov/study/NCT02951052. Feb. 14, 2024. 147 Pages, Available at https://clinicaltrials. gov/study/NCT02951052?tab=history&a=66#version-content-panel.
ClinicalTrials: "NCT02120352; A Phase IIb Study to Evaluate a Long-Acting Intramuscular Regimen for Maintenance of Virologic Suppression (Following Induction With an Oral Regimen of GSK1265744 and Abacavir/Lamivudine) in Human Immunodeficiency Virus Type 1 (HIV-1) Infected, Antiretroviral Therapy-Naive Adult Subjects," ClinicalTrials.gov [online], Jun. 6, 2017, 12 Pages, Retrieved from URL: https://clinicaltrials.gov/study/NCT02120352term=NCT02120352&rank=1&tab=history&a=25#version-content-panel.
ClinicalTrials: "NCT02120352: A Phase IIb Study to Evaluate a Long-Acting Intramuscular Regimen for Maintenance of Virologic Suppression (Following Induction With an Oral Regimen of GSK1265744 and Abacavir/Lamivudine) in Human Immunodeficiency Virus Type 1 (HIV-1) Infected, Antiretroviral Therapy-Naive Adult Subjects," ViiV Healthcare, ClinicalTrials.gov [online], Version 24, Mar. 7, 2016, 32 Pages.
ClinicalTrials: "NCT02938520: Study to Evaluate the Efficacy, Safety, and Tolerability of Long-acting Intramuscular Cabotegravir and Rilpivirine for Maintenance of Virologic Suppression Following Switch From an Integrase Inhibitor in HIV-1 Infected Therapy Naive Participants." ClinicalTrials.gov Identifier [online], First posted Oct. 19, 2016, 83 Pages, Retrieved from URL: https://clinicaltrials.gov/study/NCT02938520tab=history&a=1#version-content- panel.
ClinicalTrials: "NCT02951052: Study Evaluating the Efficacy, Safety, and Tolerability of Switching to Long-acting Cabotegravir Plus Long-acting Rilpivirine From Current Antiretroviral Regimen in Virologically Suppressed HIV-1-infected Adults," ClinicalTrials.gov Identifier [Online], First posted on Nov. 1, 2016, 16 Pages, Retrieved from URL: https://clinicaltrials.gov/study/NCT02951052term=nct02951052&rank=1&tab=history&a=1#version-content-panel.
clinicaltrials.gov: A Phase IIb Study to Evaluate a Long-Acting Intramuscular Regimen for Maintenance of Virologic Suppression (Following Induction With an Oral Regimen of GSK1265744 and Abacavir/Lamivudine) in Human Immunodeficiency Virus Type 1 (HIV-1) Infected, Antiretroviral Therapy-Naive Adult Subjects, Trials.gov Identifier: NCT02120352, First Posted: Apr. 22, 2014, 29 Pages, [Retrieved on Feb. 10, 2022] Retrieved from URL: https://clinicaltrials.gov/study/NCT02120352?term=NCT02120352&rank=1&tab=history&a=1#version- content-panel.
Crane H.M., et al., "A Comparison of Adherence Timeframes Using Missed Dose Items and Their Associations With Viral Load in Routine Clinical Care: is Longer Better?," AIDS and Behavior, 2017, vol. 21, pp. 470-480, Published Online On: Oct. 6, 2016.
International Search Report and Written Opinion for International Application No. PCT/IB2018/055349, mailed Oct. 8, 2018, 9 Pages.
Johnson & Johnson Press Release: "First Regimen Combining Long Acting Injectable Antiretrovirals; 32-Week LATTE 2 Study Results Presented at CROI," Johnson & Johnson, Feb. 24, 2016, 5 Pages.
Margolis D., et al., "THAB0206LB: Cabotegravir + Rilpivirine as Long-Acting Maintenance Therapy: LATTE-2 Week 48 Results," Journal of the International Aids Society, Biomed Central Ltd, London, UK, Jul. 22, 2016, vol. 19, No. Suppl 5, 1 Page, ISSN: 1758-2652.
Margolis D.A., et al., "Cabotegravir + Rilpivirine as Long-Acting Maintenance Therapy: LATTE-2 Week 48 Results," International AIDS Conference, Jul. 18-22, 2016, pp. 1-10.
Margolis D.A., et al., "Cabotegravir+Rilpivirine as Long-acting Maintenance Therapy: LATTE-2 Week 32 Results," Abstracts: CROI 2016 Conference on Retroviruses and Opportunistic Infections, Oral Abstracts, Boston, Massachusetts, Feb. 22-25, 2016, p. 10 (31 lb), pp. 2-159 (160 Pages).
Margolis D.A., et al., "Cabotegravir+Rilpivirine as Long-acting Maintenance Therapy: LATTE-2 Week 32 Results," VIIV Healthcare, 23rd Conference on Retroviruses and Opportunistic Infections, Feb. 22-25, 2016, 36 Pages.
Margolis D.A., et al., "Long-Acting Antiviral Agents for HIV Treatment," Current Opinion in HIV and AIDS, Lippincott Williams & Wilkins, US, Jul. 1, 2015, vol. 10, No. 4, pp. 246-252, ISSN: 1746-630X.
Murray M., et al., "Satisfaction, Tolerability, and Acceptability of Cabotegravir (CAB) + Rilpivirine (RPV) Long-Acting Therapy: LATTE-2 Results," 21st International AIDS Conference, Poster, col. 1, col. 2, Fig. 1, Jul. 18-22, 2016, 1 Page.
Murray M., et al., "Satisfaction, Tolerability, and Acceptability of Cabotegravir (CAB)+ Rilpivirine (RPV) Long-Acting Therapy: LATTE-2 Results Acknowledgment," 21st International AIDS Conference, Jul. 21, 2016, vol. 18, 17 Pages.
Office Action for European Application No. 18749568.4, mailed Jun. 9, 2022, 9 Pages.
Palella F.J., et al., "Declining Morbidity and Mortality Among Patients With Advanced Human Immunodeficiency Virus Infection," The New England Journal of Medicine, Mar. 26, 1998, vol. 338, No. 13, pp. 853-860.

(56) References Cited

OTHER PUBLICATIONS

R.K.R. Rajoli et al., In Silico Dose Prediction for Long-Acting Rilpivirine and Cabotegravir Administration to Children and Adolescents. Clin Pharmacokinet (2018) 57:255-266, published online May 24, 2017.
Rusconi S., et al., "Long-acting Agents for HIV Infection: Biological Aspects, Role in Treatment and Prevention, and Patient's Perspective," New Microbiological, Apr. 2017, vol. 40, No. 2, pp. 75-79.
Third Party Observation for International Application No. PCT/IB2018/055349, dated Nov. 21, 2019, 3 Pages.
VIIV Press Release: "ViiV Healthcare Announces Positive Headline Results From a Study of Two Drug Injectable Regimen for HIV Maintenance Therapy," VIIV, Nov. 3, 2015, 1 Page.
VIIV Press Release., "ViiV Healthcare to Progress Collaboration With Janssen to Develop the First Long-acting Two Drug Injectable Regimen for Treatment of HIV," VIIV, Jan. 7, 2016, 4 Pages.
W. Spreen et al., "Pharmacokinetics, safety, and tolerability with repeat doses of GSK1265744 and rilpivirine (TMC278) long-acting nanosuspensions in healthy adults", JAcquirImmune Defic Syndr, (Dec. 15, 2014), vol. 67, No. 5, pp. 487-492.
Whitfield T., et al., "Profile of Cabotegravir and its Potential in the Treatment and Prevention of HIV-I Infection: Evidence to Date," HIV/AIDS, Auckland, N.Z, Jan. 1, 2016, vol. 8,pp. 157-164, ISSN: 1179-1373.
Wikipedia: "Cabotegravir/Rilpivirine," Jun. 1, 2022, pp. 1-5, XP055927572.
Witty A., "Innovative Pipeline," GSK R & D Event, Full Presentation, Nov. 3, 2015, 137 Pages.

* cited by examiner

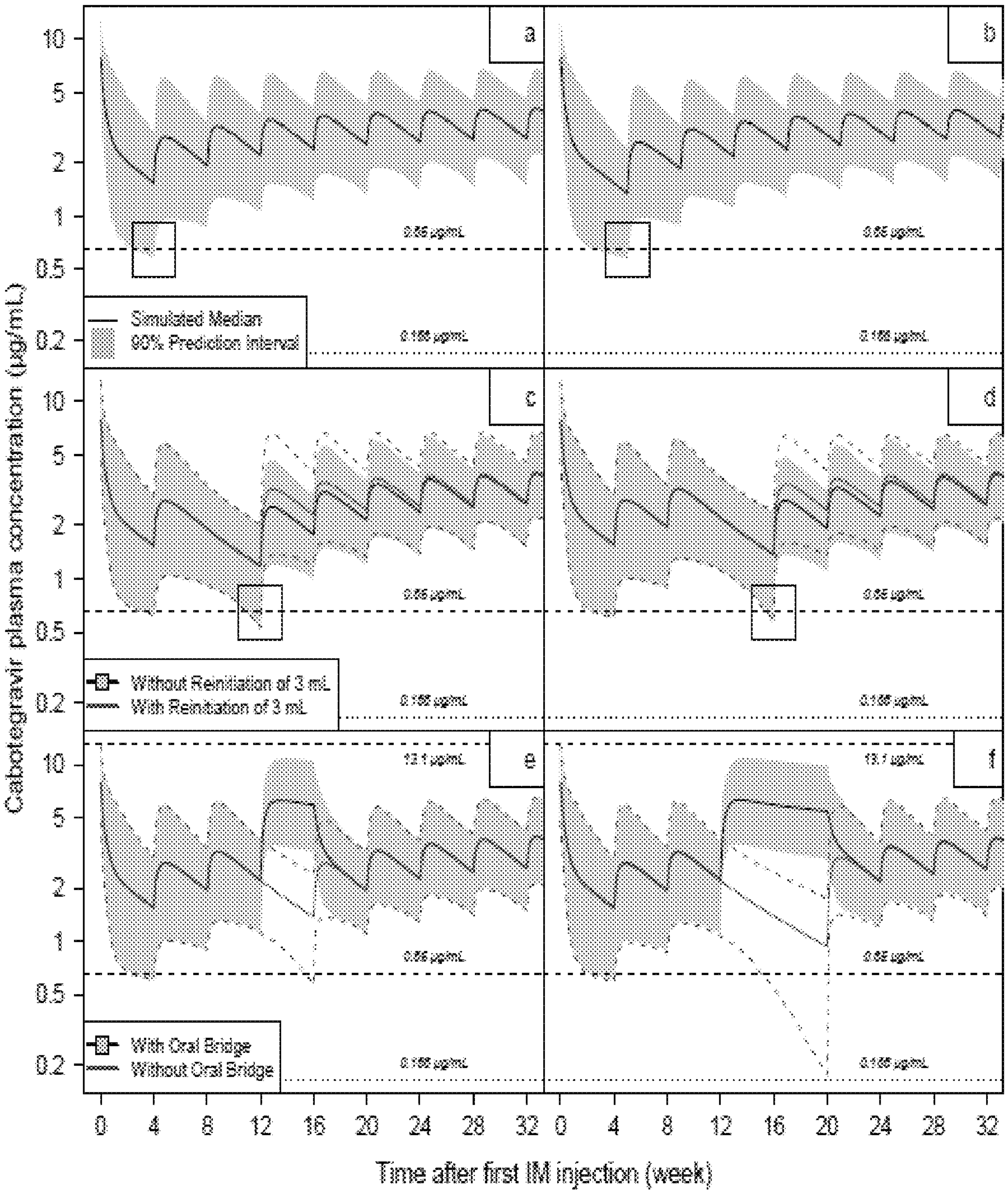
a
b
c
d
e
f
Simulated Median
90% Prediction Interval
Without Reinitiation of 3 mL
With Reinitiation of 3 mL
With Oral Bridge
Without Oral Bridge
0.65 μg/mL
0.166 μg/mL
13.1 μg/mL
Cabotegravir plasma concentration (μg/mL)
Time after first IM injection (week)

METHOD FOR TREATING HIV WITH CABOTEGRAVIR AND RILPIVIRINE

CROSS-REFERENCE TO RELATED APPLICATIONS

This application is a Continuation of U.S. application Ser. No. 17/763,076 filed Mar. 23, 2022, which is a 371 of International Application No. PCT/IB2020/059185 filed Oct. 1, 2020, which claims the benefit of the following U.S. Provisional Applications: U.S. Provisional Application No. 62/908,882 filed Oct. 1, 2019; U.S. Provisional Application No. 62/908,995, filed Oct. 1, 2019; U.S. Provisional Application No. 63/037,782 filed Jun. 11, 2020; and U.S. Provisional Application No. 63/052,214 filed Jul. 15, 2020, the disclosures of which are incorporated herein in their entireties.

FIELD OF THE INVENTION

This invention relates to a method of treating HIV in a human by the in vivo administration of cabotegravir or a pharmaceutically acceptable salt thereof, in combination with rilpivirine or a pharmaceutically acceptable salt thereof.

BACKGROUND OF THE INVENTION

The contemporary standard of care for first-line treatment of HIV-1 infection in adults naive to antiretroviral therapy (ART) is a regimen of ≥3 antiretroviral agents that includes two nucleoside reverse transcriptase inhibitors (NRTIs) and one other drug from either the boosted protease inhibitor (PI), integrase strand transfer inhibitor (INSTI), or non-nucleoside reverse transcriptase inhibitor (NNRTI) classes. However, concerns exist regarding the need for lifelong therapy with drugs that have diverse safety and tolerability profiles. Thus, 2-drug regimens (2DRs) capable of inducing and/or maintaining virologic suppression while decreasing lifetime cumulative drug exposure and potential long-term toxicities would represent an alternative treatment option for people living with HIV-1 infection.

Trials evaluating early (2000-2014) 2DRs yielded inconclusive results, perhaps partially because of small sample sizes, short treatment durations, and limitations of available treatments. The AIDS Clinical Trials Group Study A5142 team found that the virologic efficacy of a 2DR comprising efavirenz plus ritonavir-boosted lopinavir (n=250) was similar to that of efavirenz plus 2 NRTIs (n=250) through 96 weeks of treatment in ART-naive participants. However, this 2DR was associated with increased incidence of drug resistance. Likewise, the PROGRESS study demonstrated that a 2DR of ritonavir-boosted lopinavir plus raltegravir (n=101) exerts a similar antiviral effect in ART-naive participants through Week 96 compared with the 3-drug regimen (3DR) of ritonavir-boosted lopinavir plus tenofovir disoproxil fumarate/emtricitabine (n=105), but this study mostly enrolled participants with viral loads <100,000 copies/mL and CD4+ cell counts ≥200 cells/mm. The GARDEL study demonstrated the non-inferior virologic efficacy of open-label ritonavir-boosted lopinavir plus lamivudine (n=214) compared with ritonavir-boosted lopinavir plus 2 NRTIs (n=202) in ART-naive participants after 48 weeks of treatment. However, these 2DRs include ritonavir-boosted PIs, which are associated with a variety of metabolic syndromes and cardiovascular-related disease and may negate any anticipated benefit in terms of decreased drug exposure and cumulative toxicity. These studies illustrate both the potential of 2DRs as an option for ART and the importance of selecting drugs with appropriate and complementary virologic and clinical properties.

Cabotegravir (GSK1265744) is an analogue of the integrase strand transfer inhibitor (INSTI) dolutegravir that exhibits subnanomolar potency and antiviral activity against a broad range of HIV-1 strains. Oral administration of cabotegravir once daily has exhibited acceptable safety and tolerability profiles, a long half-life (40 h), and few drug-drug interactions. Rilpivirine (TMC278) is a non-nucleoside reverse transcriptase inhibitor (NNRTI) that is approved as a 25 mg once-daily oral medication for HIV-1 treatment.

In the LATTE-2 trial, patients were first put on a regimen of oral cabotegravir and abacavir/lamivudine for 20 weeks. After the induction period, suppressed patients were randomized 2:2:1 to receive either the long-acting injectable cabotegravir and rilpivirine every 4 or every 8 weeks, or to continue the 3-drug oral regimen. Patients on the long-acting regimen were extended through to 160 weeks and patients on the oral regimen were given the option of transitioning to the regimen every 4 or every 8 weeks at week 96. At 160 weeks, 104 of 115 participants (90%) and 95 of 115 participants (83%) receiving the injectable regimen, every 8 and 4 weeks respectively, remained virally suppressed.

SUMMARY OF THE INVENTION

This invention comprises a method of treating HIV in a human in need thereof which comprises the administration of a therapeutically effective amount of a combination of: cabotegravir or a pharmaceutically acceptable salt thereof, and rilpivirine or a pharmaceutically acceptable salt thereof. Alternatively, an aspect of the embodiment includes use of cabotegravir or a salt thereof and rilpivirine or a salt thereof in the manufacture of a medicament for use in the treatment of HIV infection. Alternatively, an aspect of the embodiment includes cabotegravir or a salt thereof and rilpivirine or a salt thereof for use in the treatment of HIV infection.

According to first main embodiment, a combination, in particular a 2-drug co-packaged product of cabotegravir, a human immunodeficiency virus type-1 (HIV-1) integrase strand transfer inhibitor (INSTI), and rilpivirine, an HIV-1 non-nucleoside reverse transcriptase inhibitor (NNRTI), (collectively "the Combination") is indicated as a complete regimen for the treatment of HIV-1 infection in adults to replace the current antiretroviral regimen in those who are virologically suppressed (HIV-1 RNA less than 50 copies per mL) and who have no known or suspected resistance to either cabotegravir or rilpivirine. According to an embodiment, there is provided cabotegravir or a salt thereof and rilpivirine or a salt thereof for use in the treatment of HIV infection in adults as a complete regimen to replace the current antiretroviral regimen in those who are virologically suppressed (HIV-1 RNA less than 50 copies per mL) and who have no known or suspected resistance to either cabotegravir or rilpivirine. According to an embodiment, there is provided cabotegravir or a salt thereof and rilpivirine or a salt thereof for use in the treatment of HIV infection in adults as a complete regimen to replace the current antiretroviral regimen in those who are virologically suppressed (HIV-1 RNA less than 50 copies per mL) and who have no known or suspected resistance to either cabotegravir or rilpivirine and who have no prior virological failure with agents of the NNRTI and INSTI class. According to an embodiment, there is provided cabotegravir or a salt thereof for use in the treatment of HIV infection in adults as a complete regimen to replace the current antiretroviral regimen in those who are virologically suppressed (HIV-1 RNA less than 50 copies per mL) and who have no known or suspected resistance to either cabotegravir or rilpivirine, wherein cabotegravir or a salt thereof is used in combination with rilpivirine or a salt thereof. According to an embodiment, there is provided cabotegravir or a salt thereof for use in the treatment of HIV infection in adults as a complete regimen to replace the current antiretroviral regimen in those who are virologically suppressed (HIV-1 RNA less than 50 copies per mL) and who have no known or suspected resistance to either cabotegravir or rilpivirine and who have no prior virological failure with agents of the NNRTI and INSTI class, wherein cabotegravir or a salt thereof is used in combination with rilpivirine or a salt thereof. According to an embodiment, there is provided rilpivirine or a salt thereof for use in the treatment of HIV infection in adults as a complete regimen to replace the current antiretroviral regimen in those who are virologically suppressed (HIV-1 RNA less than 50 copies per mL) and who have no known or suspected resistance to either cabotegravir or rilpivirine, wherein rilpivirine or a salt thereof is used in combination with cabotegravir or a salt thereof. According to an embodiment, there is provided rilpivirine or a salt thereof for use in the treatment of HIV infection in adults as a complete regimen to replace the current antiretroviral regimen in those who are virologically suppressed (HIV-1 RNA less than 50 copies per mL) and who have no known or suspected resistance to either cabotegravir or rilpivirine and who have no prior virological failure with agents of the NNRTI and INSTI class, wherein rilpivirine or a salt thereof is used in combination with cabotegravir or a salt thereof.

According to a second main embodiment, a method of treating HIV-1 is provided, comprising regularly administering intramuscular injections of cabotegravir or a salt thereof and rilpivirine or a salt thereof, subsequent to at least one said intramuscular injection of each of cabotegravir or a salt thereof and rilpivirine or a salt thereof, discontinuing one or both of said regularly administered intramuscular injections, and replacing the one or more discontinued intramuscular injection with regularly administered oral therapy. Alternatively, according to an aspect of this embodiment, there is provided cabotegravir or a salt thereof and rilpivirine or a salt thereof for use in therapy, in particular in the treatment of HIV infection, wherein said therapy, in particular the treatment of HIV infection, comprises regularly administering intramuscular injections of said cabotegravir or a salt thereof and rilpivirine or a salt thereof, subsequent to at least one said intramuscular injection of each of cabotegravir or a salt thereof and rilpivirine or a salt thereof, discontinuing one or both of said regularly administered intramuscular injections, and replacing the one or more discontinued intramuscular injection with regularly administered oral therapy.

According to a third main embodiment, a method of treating HIV is provided, comprising regularly administering intramuscular injections of cabotegravir or a salt thereof and rilpivirine or a salt thereof, subsequent to at least one said intramuscular injection of each of cabotegravir or a salt thereof and rilpivirine or a salt thereof, discontinuing one or both of said regularly administered intramuscular injections, and reestablishing intramuscular administration of the one or both cabotegravir or a salt thereof and rilpivirine or a salt thereof by first administering a loading dose of the discontinued cabotegravir or a salt thereof and/or rilpivirine or a salt thereof, and then continuing the regular administration of the intramuscular injections. Alternatively, according to an aspect of this embodiment, there is provided cabotegravir or a salt thereof and rilpivirine or a salt thereof for use in therapy, in particular in the treatment of HIV infection, wherein the therapy, in particular the treatment of HIV infection, comprises regularly administering intramuscular injections thereof subsequent to at least one said intramuscular injection of each of cabotegravir or a salt thereof and rilpivirine or a salt thereof, discontinuing one or both of said regularly administered intramuscular injections, and reestablishing intramuscular administration of the one or both cabotegravir or a salt thereof and rilpivirine or a salt thereof, by first administering a loading dose of the discontinued cabotegravir or a salt thereof and/or rilpivirine or a salt thereof, and then continuing the regular administration of the intramuscular injections.

BRIEF DESCRIPTION OF THE DRAWINGS

FIG. 1 depicts results of simulations as described further in Example 2.

DETAILED DESCRIPTION OF THE INVENTION

First Main Embodiment

According to first main embodiment, a combination, in particular a 2-drug co-packaged product of cabotegravir, a human immunodeficiency virus type-1 (HIV-1) integrase strand transfer inhibitor (INSTI), and rilpivirine, an HIV-1 non-nucleoside reverse transcriptase inhibitor (NNRTI), (collectively “the Combination”) is indicated as a complete regimen for the treatment of HIV-1 infection in adults to replace the current antiretroviral regimen in those who are virologically suppressed (HIV-1 RNA less than 50 copies per mL) and who have no known or suspected resistance to either cabotegravir or rilpivirine. In one embodiment, the Combination consists of a cabotegravir long-acting formulation and a rilpivirine long acting formulation. In one embodiment, the Combination consists of a cabotegravir long-acting intramuscular injection and a rilpivirine long acting intramuscular injection.

The Combination is indicated as a complete regimen for the treatment of human immunodeficiency virus type 1 (HIV-1) infection in adults to replace the current antiretroviral regimen in those who are virologically suppressed (HIV-1 RNA less than 50 copies per mL) and who have no known or suspected resistance to either cabotegravir or rilpivirine. In an embodiment, the Combination is indicated as a complete regimen for the treatment of human immunodeficiency virus type 1 (HIV-1) infection in adults to replace the current antiretroviral regimen in those who are virologically suppressed (HIV-1 RNA less than 50 copies per mL) and who have no known or suspected resistance to either cabotegravir or rilpivirine and who have no prior virological failure with agents of the NNRTI and INSTI class.

According to an aspect of the main embodiment, oral lead-in dosing to assess tolerability of the combination, where an oral lead-in (one 30-mg tablet of cabotegravir and one 25-mg tablet of rilpivirine once daily, for instance one tablet comprising 31.62 mg cabotegravir sodium and one tablet comprising 27.5 mg rilpivirine hydrochloride) is to be used for approximately 1 month (at least 28 days) prior to the initiation of the Combination to assess the tolerability of cabotegravir and rilpivirine.

According to another aspect of the main embodiment, the Combination is administered by intramuscular injections. Specifically, Initiation Injections (3-mL Dosing Kit)

Initiate injections on the final day of oral lead-in. The recommended initial injection doses of the Combination in adults are a single 3-mL (600 mg) intramuscular injection of cabotegravir and a single 3-mL (900 mg) intramuscular injection of rilpivirine. Cabotegravir and rilpivirine should be administered at separate gluteal injection sites during the same visit.

Continuation Injections (2-mL Dosing Kit)

After the initiation injections, the recommended continuation injection doses of the Combination in adults are a single 2-mL (400 mg) intramuscular injection of cabotegravir and a single 2-mL (600 mg) intramuscular injection of rilpivirine monthly. Cabotegravir and rilpivirine should be administered at separate gluteal injection sites during the same visit. Patients may be given the Combination up to 7 days before or after the date of the monthly 2-mL injection dosing schedule.

TABLE 1

Recommended Dosing Schedule in Adults

| Drug | Oral Lead-In (at Least 28 Days) Month 1 | Intramuscular Initiation Injections (One-Time Dosing) At Month 2 (On the Last Day of Oral Lead-In Dosing) | Intramuscular Continuation Injections (Once Monthly) Month 3 Onwards |
|---|---|---|---|
| Cabotegravir | 30 mg once daily | 3 mL (600 mg) | 2 mL (400 mg) |
| Rilpivirine | 25 mg once daily | 3 mL (900 mg) | 2 mL (600 mg) |

According to another aspect of the main embodiment, adherence to the monthly injection dosing schedule is strongly recommended. Patients who miss a scheduled injection visit should be clinically reassessed to ensure resumption of therapy remains appropriate. Refer to Table 2 for dosing recommendations after missed injections.

TABLE 2

Injection Dosing Recommendations after Missed Injections or Oral Therapy

| Time Since Last Injection | Recommendation |
|---|---|
| <2 months | Continue with the monthly 2-mL injection dosing schedule as soon as possible. |
| ≥2 months | Re-initiate the patient on the 3-mL dose, and then continue to follow the monthly 2-mL injection dosing schedule. |

According to another aspect of the main embodiment, injections must be administered by a healthcare professional. A complete dose requires 2 injections: one injection of cabotegravir and one injection of rilpivirine. Injections of the Combination are intended for intramuscular use only. Consider the body mass index (BMI) of the patient to ensure that the needle length is sufficient to reach the gluteus muscle. Administer each injection at separate gluteal injection sites during the same visit. The ventrogluteal site is recommended.

According to another aspect of the main embodiment, cabotegravir and rilpivirine are suspensions for intramuscular injection that do not need further dilution or reconstitution. The administration order of cabotegravir and rilpivirine injections is not important. Before preparing the injections, remove the Combination from the refrigerator and wait at least 15 minutes to allow the medications to come to room temperature. Shake each vial of the Combination vigorously so that the suspensions look uniform before injecting. Small air bubbles are expected and acceptable. Parenteral drug products should be inspected visually for particulate matter and discoloration prior to administration whenever solution and container permit. The cabotegravir vial has a brown tint to the glass which may limit visual inspection. Discard the Combination if either medicine exhibits particulate matter or discoloration.

According to an aspect, oral lead-in is provided by cabotegravir sodium, in particular 30 mg base equivalent. According to an aspect, oral lead-in is provided by rilpivirine hydrochloride, in particular 25 mg base equivalent. According to an aspect, cabotegravir injection, in particular intramuscular injection, is provided by cabotegravir base. In an aspect, rilpivirine injection, in particular intramuscular injection, is provided by rilpivirine base.

According to another aspect of the main embodiment, the Combination contains cabotegravir 200 mg/mL as a white to light pink, free-flowing extended-release injectable suspension and rilpivirine 300 mg/mL as a white to off-white extended-release injectable suspension, co-packaged as follows:

2-mL Dosing Kit
- single-dose vial of 400 mg of cabotegravir
- single-dose vial of 600 mg of rilpivirine 3-mL Dosing Kit
- single-dose vial of 600 mg of cabotegravir
- single-dose vial of 900 mg of rilpivirine In an embodiment, the above-mentioned vials of cabotegravir and rilpivirine are not co-packed, but are packed separately.

According to another aspect of the main embodiment, the Combination is contraindicated in patients:
- with previous hypersensitivity reaction to cabotegravir or rilpivirine.
- receiving the following coadministered drugs for which significant decreases in cabotegravir and/or rilpivirine plasma concentrations may occur due to uridine diphosphate (UDP)-glucuronosyl transferase (UGT) TAT and/or cytochrome P450 (CYP)3A enzyme induction, which may result in loss of virologic response:
  - Anticonvulsants: Carbamazepine, oxcarbazepine, phenobarbital, phenytoin
  - Antimycobacterials: Rifabutin, rifampin, rifapentine
  - Glucocorticoid (systemic): Dexamethasone (more than a single-dose treatment)
  - Herbal product: St John's wort (*Hypericum perforatum*)

According to another aspect of the main embodiment, precautions are taken prior to and during treatment with the Combination. Severe skin and hypersensitivity reactions have been reported during postmarketing experience with oral rilpivirine-containing regimens including cases of Drug Reaction with Eosinophilia and Systemic Symptoms (DRESS). While some skin reactions were accompanied by constitutional symptoms such as fever, other skin reactions were associated with organ dysfunctions, including elevations in hepatic serum biochemistries. During the Phase 3 clinical trials of oral rilpivirine, treatment-related rashes with at least Grade 2 severity were reported in 3% of subjects; however, no Grade 4 rash was reported.

According to another aspect of the main embodiment, the Combination is administered by intramuscular injections alone. Specifically, the intramuscular injections are administered without following oral lead in. In an embodiment, progressing to intramuscular injections without oral lead in demonstrate similar efficacy to treatment including oral lead in prior to intramuscular injections. ART-naive participants achieving virologic suppression (HIV-1 RNA<50c/mL) with daily oral dolutegravir/abacavir/lamivudine during the 20-week Induction Phase by randomizing and administering (1:1) either continue daily oral dolutegravir/abacavir/lamivudine or switch to LA. Participants randomizing with monthly Combination therapy received an oral lead in of the Combination once daily for ≥4 weeks before receiving monthly injectable Combination. After completing the Maintenance Phase at Week (W) 100, dolutegravir/abacavir/lamivudine arm participants switched to Combination therapy (Extension Switch population) either directly (Direct to Inject [DTI] arm) or with a 4-week oral lead in. Endpoints assessed at W124 for the Extension Switch population included viral load (HIV-1 RNA ≥50c/mL and <50c/mL), confirmed virologic failure (CVF; two consecutive HIV-1 RNA ≥200c/mL), safety and tolerability aspects. Switching to Combination therapy without oral lead in demonstrated similar efficacy to treatment including oral lead in at W124. Safety and tolerability were comparable between treatment groups. This suggests the Combination, with optional oral lead in, is a well-tolerated and effective maintenance therapy for virologically suppressed patients living with HIV-1.

According to another aspect of the main embodiment, the Combination is used to treat Hepatitis C. In one embodiment, the Combination is used to treat Hepatitis C HIV co-infection. Open-label, international phase 3 studies that evaluated switching to monthly intramuscular injections of the Combination formulations of CAB (CAB LA)+RPV (RPV LA) vs continuing oral standard of care ART in adult participants with HIV-1 RNA <50 c/mL. In the Combination arm, participants initially received oral CAB 30 mg+RPV 25 mg once daily for 4 weeks, to assess safety and tolerability, before starting monthly injectable therapy. Participants with chronic HCV infection without cirrhosis who do not require HCV treatment were analyzed for proportion with plasma HIV-1 RNA >50 c/mL and <50 c/mL (Snapshot algorithm), change from baseline in CD4+ cell count, general and hepatic safety, and PK parameters. The combination demonstrated similar efficacy and safety to oral standard of care therapy in participants co-infected with HIV and HCV.

Hypersensitivity reactions have been reported in association with other integrase inhibitors. These reactions were characterized by rash, constitutional findings, and sometimes organ dysfunction, including liver injury. While no such reactions have been observed in Phase 2 and 3 clinical trials in association with cabotegravir, remain vigilant and discontinue the Combination if a hypersensitivity reaction is suspected.

Discontinue the Combination immediately if signs or symptoms of severe skin or hypersensitivity reactions develop (including, but not limited to, severe rash, or rash accompanied by fever, general malaise, fatigue, muscle or joint aches, blisters, mucosal involvement [oral blisters or lesions], conjunctivitis, facial edema, hepatitis, eosinophilia, angioedema). Clinical status, including liver transaminases, should be monitored and appropriate therapy initiated. Administer oral lead-in dosing prior to administration of the Combination to help identify patients who may be at risk of a hypersensitivity reaction.

Hepatotoxicity has been reported in a limited number of patients receiving cabotegravir with or without known preexisting hepatic disease. Hepatic adverse events have been reported in patients receiving a rilpivirine-containing tablet regimen. Patients with underlying hepatitis B or C virus infection or marked elevations in transaminases prior to treatment may be at increased risk for worsening or development of transaminase elevations. A few cases of hepatoxicity have been reported in adult patients receiving a rilpivirine-containing regimen who had no pre-existing hepatic disease or other identifiable risk factors. Monitoring of liver chemistries is recommended and treatment with the Combination should be discontinued if hepatotoxicity is suspected.

Depressive disorders (including depressed mood, depression, dysphoria, major depression, mood altered, negative thoughts, suicide attempt, and suicidal ideation or attempt) have been reported with rilpivirine. Promptly evaluate patients with severe depressive symptoms to assess whether the symptoms are related to the Combination and to determine whether the risks of continued therapy outweigh the benefits.

The concomitant use of the Combination and other drugs may result in known or potentially significant drug interactions, some of which may lead to loss of therapeutic effect of the Combination and possible development of viral resistance.

Rilpivirine at the recommended dose of 25 mg once daily is not associated with a clinically relevant effect on QTc. Rilpivirine plasma concentrations after rilpivirine injections are comparable to those during therapy which do not prolong the QTc interval. In healthy subjects, 75 mg once daily and 300 mg once daily of oral rilpivirine have been shown to prolong the QTc interval of the electrocardiogram. The Combination should be used with caution in combination with drugs that are known to have a risk of Torsade de Pointes.

See Table 5 for steps to prevent or manage these possible and known significant drug interactions, including dosing recommendations. Consider the potential for drug interactions prior to and during therapy with the Combination; review concomitant medications during therapy with the Combination.

Residual concentrations of cabotegravir and rilpivirine may remain in the systemic circulation of patients for prolonged periods (up to 12 months or longer). Consider the long-acting characteristics of cabotegravir and rilpivirine when the Combination is discontinued.

To minimize the risk of developing viral resistance, it is essential to adopt an alternative, fully suppressive antiretroviral regimen no later than 1 month after the final injection doses of the Combination. If virologic failure is suspected, prescribe an alternative regimen as soon as possible.

According to another aspect of the main embodiment, because clinical trials are conducted under widely varying conditions, adverse reaction rates observed in the clinical trials of a drug cannot be directly compared with rates in the clinical trials of another drug and may not reflect rates observed in practice.

The safety assessment of the Combination is based on the analysis of pooled 48-week data from 1,182 virologically suppressed subjects with HIV-1 infection in 2 international, multicenter, open-label pivotal trials, FLAIR and ATLAS. Additional safety information from earlier clinical trials in the cabotegravir and rilpivirine program have been considered in assessing the overall safety profile of the Combination.

Adverse reactions were reported following exposure to the Combination extended-release injectable suspensions (median time exposure: 54 weeks) and data from cabotegravir tablets and rilpivirine tablets administered in combination as oral lead-in therapy (median time exposure: 5.3 weeks). Adverse reactions include those attributable to both the oral and injectable formulations of cabotegravir and rilpivirine administered as a combination regimen.

The most common adverse reactions regardless of severity reported in ≥2% of adult subjects in the pooled analyses from FLAIR and ATLAS are presented in Table 3. No adverse reactions of Grade 5 occurred in subjects treated with cabotegravir plus rilpivirine. Selected laboratory abnormalities are included in Table 4.

Non-injection-site-related adverse events leading to discontinuation and occurring in more than 1 subject were hepatitis A, acute hepatitis B, headache, and diarrhea which occurred with an incidence of ≤1%.

TABLE 3

Adverse Reactions[a] (Grades 1 to 4) Reported in at Least 2% of Virologically Suppressed Subjects with HIV-1 Infection in FLAIR and ATLAS Trials (Week 48 Pooled Analyses)

| | Cabotegravir plus Rilpivirine (n = 591) | | Current Antiretroviral Regimen (n = 591) | |
|---|---|---|---|---|
| Adverse Reactions | All Grades | At Least Grade 2 | All Grades | At Least Grade 2 |
| Injection site reactions[b] | 81% | 37% | 0 | 0 |
| Pyrexia[c] | 8% | 2% | 0 | 0 |
| Fatigue[d] | 5% | 1% | <1% | <1% |
| Headache | 4% | <1% | <1% | <1% |
| Musculoskeletal pain[e] | 3% | 1% | <1% | 0 |
| Nausea | 3% | <1% | 1% | <1% |
| Sleep disorders[f] | 2% | <1% | <1% | 0 |
| Dizziness | 2% | <1% | <1% | 0 |

[a]Adverse reactions defined as "treatment-related" as assessed by the investigator.

[b]See below for additional information on injection site reactions.

[c]Pyrexia: includes pyrexia, feeling hot, chills, influenza-like illness, body temperature increased.

[d]Fatigue: includes fatigue, malaise, asthenia.

[e]Musculoskeletal pain: includes musculoskeletal pain, musculoskeletal discomfort, back pain, myalgia, pain in extremity.

[f]Sleep disorders: includes insomnia, poor quality sleep, somnolence.

The following adverse reactions (Grades 2 to 4) occurred in <1% of subjects receiving cabotegravir plus rilpivirine: Gastrointestinal Disorders: Abdominal pain (including upper abdominal pain), diarrhea, flatulence, nausea, vomiting, General Disorders and Administration Site Conditions: Asthenia, fatigue, malaise, Hepatobiliary Disorders: Hepatotoxicity. No cases of hepatotoxicity were observed in the pivotal Phase 3 trials. Cases were identified with cabotegravir in Phase 1 and 2 trials, Investigations: Weight increase. At Week 48, subjects in FLAIR and ATLAS who received cabotegravir plus rilpivirine had a median weight gain of 1.5 kg; those in the current antiretroviral regimen group had a median weight gain of 1.0 kg (pooled analysis). In the individual FLAIR and ATLAS trials, the median weight gain in subjects receiving cabotegravir plus rilpivirine were 1.3 kg and 1.8 kg respectively, compared with 1.5 kg and 0.3 kg in subjects receiving current antiretroviral regimen, Musculoskeletal and Connective Tissue Disorders: Myalgia, Nervous System Disorders: Dizziness, headache, Psychiatric Disorders: Anxiety, depression, insomnia, Skin and Subcutaneous Tissue Disorders: Rash (including rash erythematous, rash generalized, rash macular, rash maculo-papular, rash morbilliform, rash papular, rash pruritic). The following Grade 1 adverse reactions occurred in subjects receiving cabotegravir plus rilpivirine: Nervous System Disorders: Somnolence (<1%), Psychiatric Disorders: Abnormal dreams (1%).

Local ISRs (injection site reactions) were the most frequent adverse events associated with the intramuscular administration of the Combination. After 14,682 injections, 3,663 ISRs were reported. The percentage of subjects reporting ISRs decreased over time (Week 4, 70% and Week 48, 16%). A total of 1% of subjects in FLAIR and ATLAS discontinued treatment with the Combination because of ISRs. In FLAIR and ATLAS at the Week 48 analysis, 84% of subjects had at least 1 local ISR at some point over the analysis period, consisting primarily of localized pain/discomfort (79%); based on all grades irrespective of relatedness. Other manifestations of ISRs reported in more than 1% of subjects over the duration of the analysis period included nodules (14%), induration (12%), swelling (8%), erythema (4%), pruritus (4%), bruising (3%), warmth (2%), and hematoma (2%). Abscess and cellulitis at the injection site were each reported in <1% of subjects. The severity of ISRs was generally mild (Grade 1, 75%) or moderate (Grade 2, 36%). Four percent (4%) of subjects experienced severe (Grade 3) ISRs, and no subjects experienced Grade 4 ISRs. The median duration of ISR events was 3 days. The percentage of subjects reporting ISRs decreased over time (Week 4, 70% and Week 48, 16%).

Selected laboratory abnormalities with a worsening grade from baseline and representing the worst-grade toxicity are presented in Table 4.

TABLE 4

Selected Laboratory Abnormalities (Grades 3 to 4; Week 48 Pooled Analyses) in FLAIR and ATLAS Trials

| Laboratory Parameter Preferred Term | Cabotegravir plus Rilpivirine (n = 591) | Current Antiretroviral Regimen (n = 591) |
|---|---|---|
| ALT (>5.0 × ULN) | 2% | <1% |
| AST (>5.0 × ULN) | 2% | <1% |
| Bilirubin (>2.5 × ULN) | <1% | <1% |
| Creatine phosphokinase (≥10.0 × ULN) | 8% | 4% |
| Lipase (>3.0 × ULN) | 5% | 3% |

ULN = Upper limit of normal.

Changes in Transaminases: A few subjects had transaminase elevations attributed to suspected hepatotoxicity in relation to oral cabotegravir exposure in Phase 1 and 2 trials. Elevated transaminases (AST/ALT) were observed in subjects receiving cabotegravir plus rilpivirine during the pivotal Phase 3 trials; however, the primary reason for these elevations was the occurrence of acute viral hepatitis (Hepatitis A, B, or C).

Changes in Total Bilirubin: Small, non-progressive increases in total bilirubin (without clinical jaundice) were observed with cabotegravir plus rilpivirine. These changes are not considered clinically relevant as they likely reflect competition between cabotegravir and unconjugated bilirubin for a common clearance pathway (UGT1A1).

Changes in Creatine Phosphokinase (CPK): Asymptomatic CPK elevations, mainly in association with exercise, have also been reported with cabotegravir plus rilpivirine.

The following adverse reactions have been identified during postmarketing experience in patients receiving an oral rilpivirine-containing regimen. Because these reactions are reported voluntarily from a population of uncertain size, it is not always possible to reliably estimate their frequency or establish a causal relationship to drug exposure: Severe skin and hypersensitivity reactions, including DRESS.

According to another aspect of the main embodiment, coadministration of the Combination with other medications should be monitored or avoided.

Because the Combination is a complete regimen, coadministration with other antiretroviral medications for the treatment of HIV-1 infection is not recommended. There are no limitations on the use of other antiretroviral medications after discontinuing the Combination.

Cabotegravir is primarily metabolized by UGT1A1 with some contribution from UGT1A9. Drugs which are strong inducers of UGT1A1 or 1A9 are expected to decrease cabotegravir plasma concentrations and may result in loss of virologic response; therefore, coadministration with these drugs is contraindicated. Simulations using physiologically based pharmacokinetic (PBPK) modeling show that no clinically significant interaction is expected during coadministration of cabotegravir with drugs that inhibit these enzymes.

non-nucleoside reverse transcriptase inhibitors (NNRTIs). Coadministration of the Combination and drugs that inhibit CYP3A may result in increased plasma concentrations of rilpivirine.

QT-Prolonging Drugs: Oral rilpivirine at the recommended dose of 25 mg once daily is not associated with a clinically relevant effect on QTc. Plasma rilpivirine concentrations after rilpivirine injections are comparable to those during rilpivirine therapy. In healthy subjects, 75-mg and 300-mg once daily oral doses of rilpivirine have been shown to prolong the QTc interval of the electrocardiogram. The Combination should be used with caution in combination with drugs with a known risk of Torsade de Pointes.

Information regarding potential drug interactions with cabotegravir and rilpivirine are provided in Table 5. These recommendations are based on either drug interaction trials following oral administration of the individual components or predicted interactions due to the expected magnitude of the interaction and potential for loss of efficacy.

TABLE 5

Established and Other Potentially Significant Drug Interactions

| Concomitant Drug Class: Drug Name | Effect on Concentration | Clinical Comment |
|---|---|---|
| Anticonvulsants: Carbamazepine Oxcarbazepine Phenobarbital Phenytoin | ↓Cabotegravir ↓Rilpivirine | Coadministration is contraindicated with the combination due to potential for loss of therapeutic effect and development of resistance [see Contraindications (4)]. |
| Antimy cobacterials: Rifampin[a] Rifapentine | ↓Cabotegravir ↓Rilpivirine | |
| Antimy cobacterial: Rifabutin[a] | ↓Cabotegravir ↔Rifabutin ↓Rilpivirine | |
| Glucocorticoid (systemic): Dexamethasone (more than a single-dose treatment) | ↓Rilpivirine | |
| Herbal Product: St John's wort (*Hypericum perforatum*) | ↓Rilpivirine | |
| Macrolide or ketolide antibiotics: Clarithromycin Erythromycin Telithromycin | ↔Cabotegravir ↑Rilpivirine | Where possible, consider alternatives, such as azithromycin. |
| Narcotic analgesic: Methadone[a] | ↔Cabotegravir ↓Methadone ↔Rilpivirine | No dose adjustment is required when starting coadministration of methadone with the combination. However, clinical monitoring is recommended as methadone maintenance therapy may need to be adjusted in some patients. |

↑ = Increase,
↓ = Decrease,
↔ = No change.

Cabotegravir is a substrate of breast cancer resistance protein (BCRP) and P-glycoprotein (P-gp) in vitro; however, because of its high permeability, no alteration in cabotegravir absorption is expected when coadministered with BCRP or P-gp inhibitors.

Rilpivirine is primarily metabolized by CYP3A, and drugs that induce or inhibit CYP3A may affect the clearance of rilpivirine. Coadministration of the Combination and drugs that induce CYP3A may result in decreased plasma concentrations of rilpivirine and loss of virologic response and possible resistance to rilpivirine or to the class of Based on drug interaction study results, the following drugs can be coadministered with cabotegravir without a dose adjustment: etravirine, midazolam, oral contraceptives containing levonorgestrel and ethinyl estradiol, and rilpivirine.

Based on drug interaction study results, the following drugs can be coadministered with rilpivirine: acetaminophen, atorvastatin, cabotegravir, chlorzoxazone, dolutegravir, ethinyl estradiol, norethindrone, raltegravir, ritonavir-boosted atazanavir, ritonavir-boosted darunavir, sildenafil, tenofovir alafenamide, and tenofovir disoproxil fumarate.

Rilpivirine did not have a clinically significant effect on the pharmacokinetics of digoxin or metformin. No clinically relevant drug-drug interaction is expected when rilpivirine is coadministered with maraviroc, ribavirin, or the nucleoside reverse transcriptase inhibitors (NRTIs) abacavir, emtricitabine, lamivudine, stavudine, and zidovudine.

According to another aspect of the main embodiment, care should be taken with administration of the Combination to specific patient populations.

There is a pregnancy exposure registry that monitors pregnancy outcomes in women exposed to the Combination during pregnancy. There are insufficient human data on the use of the Combination during pregnancy to adequately assess a drug-associated risk of birth defects and miscarriage. Cabotegravir use in pregnant women has not been evaluated; however, rilpivirine use during pregnancy has been evaluated in over 200 first trimester exposures reported to the APR (Antiretroviral Pregnancy Register). Available data from the APR show no increase in the risk of overall major birth defects with exposure to rilpivirine during the first trimester of pregnancy compared with the background rate for major birth defects of 2.7% in a U.S. reference population of the Metropolitan Atlanta Congenital Defects Program (MACDP).

The rate of miscarriage is under-reported in the APR. The background risk for major birth defects and miscarriage for the indicated population is unknown. The estimated background rate of miscarriage in clinically recognized pregnancies in the U.S. general population is 15% to 20%. The APR uses the MACDP as the U.S. reference population for birth defects in the general population. The MACDP evaluates women and infants from a limited geographic area and does not include outcomes for births that occurred at less than 20 weeks' gestation.

Cabotegravir and rilpivirine have been detected in systemic circulation for up to 12 months or longer after discontinuing injections of the Combination; therefore, consideration should be given to the potential for fetal exposure during pregnancy.

In animal reproduction studies, no evidence of adverse developmental outcomes was observed with oral cabotegravir in rats (>30 times the exposure at the maximum recommended human dose [MRHD] of 30 mg/day of oral cabotegravir or the 400-mg intramuscular injection dose) or in rabbits (exposure 0.66 times the MRHD of 30 mg/day of oral cabotegravir or exposure ~1 times the 400-mg intramuscular injection dose). Likewise, with oral rilpivirine, there were no adverse outcomes at exposures ≥12 (rats) and ≥57 (rabbits) times the exposure at the MRHD of 25 mg once daily of oral rilpivirine and of 600-mg intramuscular injection dose of rilpivirine.

Lower exposures with oral rilpivirine were observed during pregnancy. Viral load should be monitored closely if the patient remains on the Combination during pregnancy.

Human Data: Rilpivirine: Based on prospective reports to the APR of 524 exposures to oral rilpivirine during pregnancy resulting in live births, there was no difference between the overall risk of birth defects for rilpivirine compared with the background birth defect rate of 2.7% in the U.S. reference population of the MACDP. The prevalence of birth defects in live births was 0.9% (95% CI: 0.2% to 2.5%) and 1.24% (95% CI: 0.1% to 4.1%) following first and second/third trimester exposure, respectively, to rilpivirine-containing regimens. In a clinical trial, total oral rilpivirine exposures were generally lower during pregnancy compared with the postpartum period.

Animal Data: Cabotegravir: In a prenatal and postnatal development study in rats, cabotegravir was administered orally at 0.5, 5, or 1,000 mg/kg/day during organogenesis and through delivery and lactation. At 1,000 mg/kg/day (>30 times the systemic exposure at the MRHD of 30 mg/day dosed orally or the 400-mg intramuscular injection dose), cabotegravir delayed the onset of parturition, and in some rats, this delay was associated with an increased number of stillbirths and neonatal mortalities immediately after birth. There were no alterations to growth and development of surviving offspring at doses up to 1,000 mg/kg/day. When rat pups born to cabotegravir-treated dams were cross-fostered at birth and nursed by control mothers, similar incidences of neonatal mortalities were observed; there was no effect on neonatal survival of control pups nursed from birth by cabotegravir-treated mothers. A lower dose of 5 mg/kg/day of cabotegravir (exposure [AUC]>10 times the MRHD of 30 mg/day dosed orally or the 400-mg intramuscular injection dose) was not associated with delayed parturition or neonatal mortality in rats. When cabotegravir was administered orally to pregnant rats and rabbits (doses of 1,000 or 2,000 mg/kg/day, respectively) during organogenesis, there was no effect on survival when fetuses were delivered by cesarean section. No adverse effects on embryo-fetal development were observed in rabbit fetuses up to 2,000 mg/kg/day (exposure [AUC]0.66 times the MRHD of 30 mg/day dosed orally or ~1 times the 400-mg intramuscular injection dose); in rats, alterations in fetal growth (decreased body weights) in the presence of maternal toxicity (decreased body weight gain, transient reductions in food consumption) were observed at 1,000 mg/kg/day (>30 times the systemic exposure at the MRHD of 30 mg/day dosed orally or the 400-mg intramuscular injection dose); however, there were no test article-related fetal malformations or variations at any dose. Studies in pregnant rats showed that cabotegravir crosses the placenta and can be detected in fetal tissue.

Rilpivirine: Rilpivirine was administered orally to pregnant rats (40, 120, or 400 mg/kg/day) and rabbits (5, 10, or 20 mg/kg/day) through organogenesis (on Gestation Days 6 through 17, and 6 through 19, respectively). No significant toxicological effects were observed in embryo-fetal toxicity studies performed with rilpivirine in rats and rabbits at exposures ≥12 (rats) and ≥57 (rabbits) times the exposure in humans at the MRHD of 25 mg once daily or 600-mg intramuscular injection dose of rilpivirine in HIV-1-infected patients. In a prenatal and postnatal development study with rilpivirine, where rats were administered up to 400 mg/kg/day through lactation, no significant adverse effects directly related to drug were noted in the offspring.

The Centers for Disease Control and Prevention recommends that HIV-1-infected mothers in the United States not breastfeed their infants to avoid risking postnatal transmission of HIV-1 infection. It is not known if the components of the Combination are present in human breast milk, affect human milk production, or have effects on the breastfed infant. When administered to lactating rats, cabotegravir and rilpivirine were present in milk. Cabotegravir and rilpivirine could be present in human milk for 12 months or longer after the last injections have been administered.

Because of the potential for (1) HIV-1 transmission (in HIV-negative infants), (2) developing viral resistance (in HIV-positive infants), and (3) adverse reactions in a breastfed infant similar to those seen in adults, instruct mothers not to breastfeed if they are receiving the Combination.

Animal Data: Cabotegravir: In animals, no studies have been conducted to assess the secretion of cabotegravir into milk directly; however, cabotegravir was present in plasma of rat pups exposed through the milk of lactating rats (dosed up to 1,000 mg/kg/day), with mean plasma concentrations in pups of approximately 70% that of plasma concentrations occurring in pregnant female rats on Gestation Day 20.

Rilpivirine: In animals, no studies have been conducted to assess the secretion of rilpivirine into milk directly; however, rilpivirine was present in plasma of rat pups exposed through the milk of lactating rats (dosed up to 400 mg/kg/day).

Safety and efficacy of the components of the Combination have not been established in pediatric patients.

Clinical trials of the Combination did not include sufficient numbers of subjects aged 65 and older to determine whether they respond differently from younger subjects. In general, caution should be exercised in administration of the Combination in elderly patients reflecting greater frequency of decreased hepatic, renal, or cardiac function, and of concomitant disease or other drug therapy.

The Combination has not been studied in patients with renal impairment. Based on studies with oral cabotegravir and population pharmacokinetic analyses of oral rilpivirine, no dosage adjustment of the Combination is necessary for patients with mild or moderate renal impairment (creatinine clearance ≥30 mL/min) and not on dialysis. However, in patients with severe renal impairment (creatinine clearance <30 mL/min) or end-stage renal disease, the Combination should be used with caution and increased monitoring for adverse effects is recommended.

The Combination has not been studied in patients with hepatic impairment. Based on separate studies with oral cabotegravir and oral rilpivirine, no dosage adjustment of the Combination is necessary for patients with mild or moderate hepatic impairment (Child-Pugh Score A or B). The effect of severe hepatic impairment (Child-Pugh Score C) on the pharmacokinetics of cabotegravir or rilpivirine is unknown.

According to another aspect of the main embodiment, a treatment for overdosage of one or both components of the Combination is provided. There is no known specific treatment for overdose with cabotegravir or rilpivirine. If overdose occurs, the patient should be monitored and standard supportive treatment applied as required, including monitoring of vital signs and ECG (QT interval) as well as observation of the clinical status of the patient. As both cabotegravir and rilpivirine are highly bound to plasma proteins, it is unlikely that either would be significantly removed by dialysis. Consider the prolonged exposure to cabotegravir and rilpivirine (components of the Combination) following an injection when assessing treatment needs and recovery.

According to another aspect of the main embodiment, the Combination contains cabotegravir extended-release injectable suspension, an HIV INSTI, co-packaged with and rilpivirine extended-release injectable suspension, an HIV NNRTI, in particular the Combination contains cabotegravir extended-release injectable suspension, an HIV INSTI, co-packed with rilpivirine extended-release injectable suspension, an HIV NNRTI. In an embodiment, the Combination contains cabotegravir extended-release injectable suspension, an HIV INSTI, packed separately from the rilpivirine extended-release injectable suspension, an HIV NNRTI.

Cabotegravir: The chemical name for cabotegravir is (3S,11aR)-N-[(2,4-difluorophenyl)methyl]-6-hydroxy-3-methyl-5,7-dioxo-2,3,5,7,11,11a-hexahydro[1,3]oxazolo[3,2-a]pyrido[1,2-d]pyrazine-8-carboxamide. The empirical formula is $C_{19}H_{17}F_2N_3O_5$ and the molecular weight is 405.35 g/mol. It has the following structural formula:

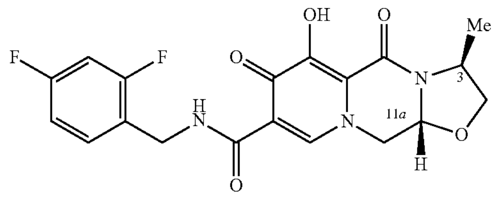 [SMILES: C[C@H]1CO[C@@H]2Cn3cc(C(=O)NCc4ccc(F)cc4F)c(=O)c(O)c3C(=O)N12]

Cabotegravir extended-release injectable suspension is a white to light pink free-flowing suspension for intramuscular injection. Each sterile single-dose vial contains the following:

2-mL Vial

Cabotegravir 400 mg and the following inactive ingredients: mannitol (70 mg), polysorbate 20 (40 mg), polyethylene glycol (PEG) 3350 (40 mg), and Water for Injection.

3-mL Vial

Cabotegravir 600 mg and the following inactive ingredients: mannitol (105 mg), polysorbate 20 (60 mg), polyethylene glycol (PEG) 3350 (60 mg), and Water for Injection.

The cabotegravir tablet contains cabotegravir, as cabotegravir sodium. Cabotegravir sodium is a white to almost white solid that is slightly soluble in water. Each immediate-release film-coated tablet of cabotegravir for oral administration contains 30 mg of cabotegravir (equivalent to 31.62 mg cabotegravir sodium) and the inactive ingredients: hypromellose, lactose monohydrate, magnesium stearate, microcrystalline cellulose, and sodium starch glycolate. The tablet film-coating contains hypromellose, polyethylene glycol, and titanium dioxide.

Rilpivirine: The chemical name for rilpivirine is 4-[[4-[[4-[(E)-2-cyanoethenyl]-2,6-dimethylphenyl]amino]-2-pyrimidinyl]amino]benzonitrile. Its molecular formula is $C_{22}H_{18}N_6$ and its molecular weight is 366.42. Rilpivirine has the following structural formula:

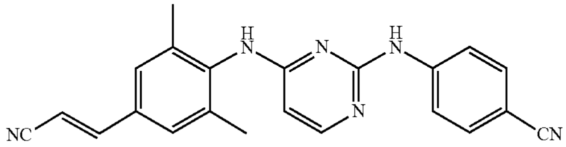 [SMILES: Cc1cc(/C=C/C#N)cc(C)c1Nc1ccnc(Nc2ccc(C#N)cc2)n1]

Rilpivirine extended-release injectable suspension is a white to off-white suspension for intramuscular injection. Each sterile single-dose vial contains the following:

2-mL Vial

Rilpivirine 600 mg and the following inactive ingredients: poloxamer 338 (100 mg), citric acid monohydrate (2 mg); glucose monohydrate, sodium dihydrogen phosphate monohydrate, sodium hydroxide to adjust pH and ensure isotonicity, and Water for Injection.

3-mL Vial

Rilpivirine 900 mg and the following inactive ingredients: poloxamer 338 (150 mg), citric acid monohydrate (3 mg); glucose monohydrate, sodium dihydrogen phosphate monohydrate, sodium hydroxide to adjust pH and ensure isotonicity, and Water for Injection.

The vial stoppers are not made with natural rubber latex.

According to another aspect of the main embodiment, the Combination exhibits certain clinical pharmacology.

The effect of the Combination on QT interval has not been studied.

Cabotegravir: In a randomized, placebo-controlled, 3-period cross-over trial, 42 healthy subjects were randomized into 6 random sequences and received 3 oral doses of placebo, cabotegravir 150 mg every 12 hours ($C_{max}$ approximately 3-fold of the 30-mg once-daily dose), and a single dose of moxifloxacin 400 mg (active control). After baseline and placebo adjustment, the maximum time-matched mean QTc change based on Fridericia's correction method (QTcF) for cabotegravir was 2.62 msec (1-sided 95% upper CI: 5.26 msec). Cabotegravir did not prolong the QTc interval over 24 hours post dose.

Rilpivirine: The effect of rilpivirine at the recommended oral dose of 25 mg once daily on the QTcF interval was evaluated in a randomized, placebo- and active-(moxifloxacin 400 mg once daily) controlled crossover trial in 60 healthy adults, with 13 measurements over 24 hours at steady state. The maximum mean time-matched (95% upper confidence bound) differences in QTcF interval from placebo after baseline correction was 2.0 (5.0) msec (i.e., below the threshold of clinical concern). When 75-mg and 300-mg once daily oral doses of rilpivirine (3 times and 12 times the recommended oral dosage, respectively) were studied in healthy adults, the maximum mean time-matched (95% upper confidence bound) differences in QTcF interval from placebo after baseline correction were 10.7 (15.3) and 23.3 (28.4) msec, respectively. Steady-state administration of rilpivirine 75 mg once daily and 300 mg once daily resulted in a mean steady-state $C_{max}$ approximately 4.4-fold and 11.6-fold, respectively, higher than the mean steady-state $C_{max}$ observed with the recommended 600-mg monthly dose of rilpivirine extended-release injectable suspension.

The pharmacokinetic properties of the components of the Combination are provided in Table 6. The multiple-dose pharmacokinetic parameters are provided in Table 7.

TABLE 6

Pharmacokinetic Properties of the Components of the Combination

| | Cabotegravir | Rilpivirine |
|---|---|---|
| **Absorption** | | |
| Tmax (days), median | 7 | 3 to 4 |
| **Distribution** | | |
| % Bound to human plasma proteins | >99.8 | 99.7 |
| Blood-to-plasma ratio | 0.5 | 0.7 |
| **Elimination** | | |
| $t_{1/2}$ (weeks) (absorption rate limited), mean | 5.6 to 11.5 | 13 to 28 |
| **Metabolism** | | |
| Metabolic pathways | UGT1A1<br>UGT1A9 (minor) | CYP3A |
| **Excretion** | | |
| Major route of elimination | Metabolism | Metabolism |
| % of dose excreted as total $^{14}C$ (unchanged drug) in urine[a] | 27 (0) | 6 (<1) |
| % of dose excreted as total $^{14}C$ (unchanged drug) in feces[a] | 59 (47) | 85 (26) |

[a]Dosing in mass balance studies: single-dose oral administration of [$^{14}C$] cabotegravir; single-dose oral administration of [$^{14}C$] rilpivirine.

TABLE 7

Multiple-Dose Pharmacokinetic Parameters following Monthly Intramuscular Injections of the Components of the Combination

| Drug | Dose | Geometric Mean (95% CI)[a] | | |
|---|---|---|---|---|
| Cabotegravir | 400-mg monthly IM injection | $AUC_{tau}$ (mcg · h/mL)<br>2,461<br>(2,413, 2,510) | $C_{max}$ (mcg/mL)<br>4.2<br>(4.1, 4.3) | $C_{trough}$ (mcg/mL)<br>2.9<br>(2.9, 3.0) |
| Rilpivirine | 600-mg monthly IM injection | $AUC_{tau}$ (ng · h/mL)<br>65,603<br>(63,756, 67,503) | $C_{max}$ (ng/mL)<br>116<br>(113, 119) | $C_{trough}$ (ng/mL)<br>82.2<br>(79.9, 84.6) |

[a]Pharmacokinetic parameter values were based on individual post-hoc estimates from separate cabotegravir and rilpivirine population pharmacokinetic models for subjects enrolled in FLAIR and ATLAS.

Cerebrospinal Fluid (CSF): Cabotegravir is present in CSF. In HIV-1-infected subjects receiving both cabotegravir extended-release injectable suspension and rilpivirine extended-release injectable suspension, the median cabotegravir CSF-to-plasma concentration ratio (n=16) was 0.304 to 0.344 (range: 0.218 to 0.449) and higher than corresponding median unbound cabotegravir concentrations in plasma 1 week following steady-state cabotegravir and rilpivirine extended-release injectable suspensions given monthly or every 2 months. Rilpivirine is present in CSF. In the same 16 subjects, the median rilpivirine CSF-to-plasma ratio was 1.07 to 1.32% (range: not quantifiable to 1.69%). Consistent with therapeutic cabotegravir and rilpivirine concentrations in the CSF, CSF HIV-1 RNA concentrations (n=16) were <50 copies/mL in 100% and <2 copies/mL in 15/16 (94%) of subjects. At the same time point, plasma HIV-1 RNA concentrations (n=18) were <50 copies/mL in 100% and <2 copies/mL in 12/18 (66.7%) of subjects.

According to another aspect of the main embodiment, pharmacokinetics varies by specific patient populations.

Pediatric Patients: The pharmacokinetics of the components of the combination have not been studied in pediatric patients.

Geriatric Patients: Population pharmacokinetic analyses indicated age had no clinically relevant effect on the pharmacokinetics of cabotegravir or rilpivirine. Pharmacokinetic data in subjects aged 65 years and older are limited.

Patients with Renal Impairment: No clinically important pharmacokinetic differences between subjects with severe renal impairment (CrCL<30 mL/min and not on dialysis) and matching healthy subjects were observed with oral cabotegravir. No dosage adjustment is necessary for patients with mild to severe renal impairment (not on dialysis). Cabotegravir has not been studied in patients requiring dialysis.

Population pharmacokinetic analyses indicated that mild renal impairment had no clinically relevant effect on the exposure of oral rilpivirine. There is limited or no information regarding the pharmacokinetics of rilpivirine in patients with moderate or severe renal impairment, end-stage renal disease, or patients requiring dialysis.

Patients with Hepatic Impairment: No clinically important pharmacokinetic differences between subjects with moderate hepatic impairment and matching healthy subjects were observed with oral cabotegravir. No dosage adjustment is necessary for patients with mild to moderate hepatic impairment (Child-Pugh Score A or B). The effect of severe hepatic impairment (Child-Pugh Score C) on the pharmacokinetics of cabotegravir has not been studied.

Rilpivirine exposure was 47% higher in subjects (n=8) with mild hepatic impairment (Child-Pugh Score A) and 5% higher in subjects (n=8) with moderate hepatic impairment (Child-Pugh Score B) compared with matched controls. The effect of severe hepatic impairment (Child-Pugh Score C) on the pharmacokinetics of rilpivirine has not been studied.

Patients with HBV/HCV Co-infection: Cabotegravir plus rilpivirine has not been studied in patients with hepatitis B co-infection. There is limited experience in patients with hepatitis C co-infection receiving cabotegravir and rilpivirine.

Gender and Race: Population pharmacokinetic analyses revealed that gender and race had no clinically relevant effect on the pharmacokinetics of cabotegravir or rilpivirine.

Polymorphisms in Drug Metabolizing Enzymes: In a meta-analysis of healthy and HIV-1-infected subject trials, HIV-infected subjects with UGT1A1 genotypes conferring poor cabotegravir metabolism had a 1.2-fold increase in mean steady-state cabotegravir AUC, $C_{max}$, and $C_{tau}$ following cabotegravir long-acting injection compared with subjects with genotypes associated with normal metabolism via UGT1A1. No dose adjustment is required in subjects with UGT1A1 polymorphisms.

Body Mass Index (BMI): Population pharmacokinetic analyses revealed no clinically relevant effect of BMI on the exposure of cabotegravir and rilpivirine; therefore, no dose adjustment is required on the basis of BMI. Consider the BMI of the patient to ensure that the needle length is sufficient to reach the gluteus muscle.

According to another aspect of the main embodiment, drug interaction studies were conducted with oral cabotegravir or oral rilpivirine, as individual components, and other drugs likely to be coadministered or commonly used as probes for pharmacokinetic interactions.

Cabotegravir is not a clinically relevant inhibitor of the following enzymes and transporters: CYP1A2, 2A6, 2B6, 2C8, 2C9, 2C19, 2D6, and 3A4; UGT1A1, 1A3, 1A4, 1A6, 1A9, 2B4, 2B7, 2B15, and 2B17; P-gp; BCRP; bile salt export pump (BSEP); organic cation transporter (OCT)1, OCT2; organic anion transporter polypeptide (OATP)1B1, OATP1B3; multidrug and toxin extrusion transporter (MATE) 1, MATE 2-K; multidrug resistance protein (MRP)2 or MRP4.

In vitro, cabotegravir inhibited renal organic anion transporters (OAT)1 ($IC_{50}$=0.81 microM) and OAT3 ($IC_{50}$=0.41 microM). However, based on PBPK modeling, no interaction with OAT substrates is expected at clinically relevant concentrations.

In vitro, cabotegravir did not induce CYP1A2, CYP2B6, or CYP3A4. Based on these data and the results of drug interaction trials, cabotegravir is not expected to affect the pharmacokinetics of drugs that are substrates of these enzymes.

Rilpivirine is primarily metabolized by CYP3A. Rilpivirine injection is not likely to have a clinically relevant effect on the exposure of drugs metabolized by CYP enzymes.

Based on their in vitro and clinical drug interaction profiles, cabotegravir and rilpivirine are not expected to alter concentrations of other antiretroviral medications including protease inhibitors, NRTIs, NNRTIs, integrase inhibitors, entry inhibitors, and ibalizumab.

Cabotegravir is primarily metabolized by UGT1A1 with some contribution from UGT1A9. Drugs which are strong inducers of UGT1A1 or 1A9 are expected to decrease cabotegravir plasma concentrations leading to lack of efficacy; therefore, coadministration with these drugs is contraindicated.

In vitro, cabotegravir was not a substrate of OATP1B1, OATP1B3, or OCT1. Cabotegravir is a substrate of P-gp and BCRP in vitro; however, because of its high permeability, no alteration in cabotegravir absorption is expected with coadministration of P-gp or BCRP inhibitors.

The effects of cabotegravir or rilpivirine on the exposure of coadministered drugs are summarized in Tables 8 and 10 and the effects of coadministered drugs on the exposure of cabotegravir or rilpivirine are summarized in Tables 9 and 11, respectively. No drug interaction studies have been performed with cabotegravir or rilpivirine extended-release suspension for injection. The drug interaction data provided is obtained from studies with oral cabotegravir or oral rilpivirine. Dosing recommendations as a result of established and other potentially significant drug-drug interactions with cabotegravir and rilpivirine are provided in Table 5.

TABLE 8

Effect of Cabotegravir on the Pharmacokinetics of Coadministered Drugs

| Coadministered Drug(s) and Dose(s) | Dose of Cabotegravir | n | Geometric Mean Ratio (90% CI) of Pharmacokinetic Parameters of Coadministered Drug with/without Cabotegravir No Effect = 1.00 | | |
|---|---|---|---|---|---|
| | | | $C_{max}$ | AUC | $C_\tau$ or $C_{24}$ |
| Ethinyl estradiol 0.03 mg once daily | 30 mg once daily | 19 | 0.92 (0.83, 1.03) | 1.02 (0.97, 1.08) | 1.00 (0.92, 1.10) |
| Levonorgestrel 0.15 mg once daily | 30 mg once daily | 19 | 1.05 (0.96, 1.15) | 1.12 (1.07, 1.18) | 1.07 (1.01, 1.15) |
| Midazolam 3 mg | 30 mg once daily | 12 | 1.09 (0.94, 1.26) | 1.10 (0.95, 1.26) | NA |
| Rilpivirine 25 mg once daily | 30 mg once daily | 11 | 0.96 (0.85, 1.09) | 0.99 (0.89, 1.09) | 0.92 (0.79, 1.07) |

CI = Confidence Interval;

n = Maximum number of subjects with data;

NA = Not available.

TABLE 9

Effect of Coadministered Drugs on the Pharmacokinetics of Cabotegravir

| Coadministered Drug(s) and Dose(s) | Dose of Cabotegravir | n | Geometric Mean Ratio (90% CI) of Cabotegravir Pharmacokinetic Parameters with/without Coadministered Drugs No Effect = 1.00 $C_{max}$ | AUC | $C_{\tau}$ or $C_{24}$ |
|---|---|---|---|---|---|
| Etravirine 200 mg twice daily | 30 mg once daily | 12 | 1.04 (0.99, 1.09) | 1.01 (0.96, 1.06) | 1.00 (0.94, 1.06) |
| Rifabutin 300 mg once daily | 30 mg once daily | 12 | 0.83 (0.76, 0.90) | 0.77 (0.74, 0.83) | 0.74 (0.70, 0.78) |
| Rifampin 600 mg once daily | 30 mg single dose | 15 | 0.94 (0.87, 1.02) | 0.41 (0.36, 0.46) | NA |
| Rilpivirine 25 mg once daily | 30 mg once daily | 11 | 1.05 (0.96, 1.15) | 1.12 (1.05, 1.19) | 1.14 (1.04, 1.24) |

CI = Confidence Interval;
n = Maximum number of subjects with data;
NA = Not available.

TABLE 10

Effect of Rilpivirine on the Pharmacokinetics of Coadministered Drugs

| Coadministered Drug(s) and Dose(s) | Dose of Rilpivirine | n | Geometric Mean Ratio (90% CI) of Coadministered Drug Pharmacokinetic Parameters with/without EDURANT No Effect = 1.00 $C_{max}$ | AUC | $C_{min}$ |
|---|---|---|---|---|---|
| Acetaminophen 500-mg single dose | 150 mg once daily[a] | 16 | 0.97 (0.86 to 1.10) | 0.91 (0.86 to 0.97) | NA |
| Atorvastatin 40 mg once daily | 150 mg once daily[a] | 16 | 1.35 (1.08 to 1.68) | 1.04 (0.97 to 1.12) | 0.85 (0.69 to 1.03) |
| 2-hydroxy-atorvastatin | | | 1.58 (1.33 to 1.87) | 1.39 (1.29 to 1.50) | 1.32 (1.10 to 1.58) |
| 4-hydroxy-atorvastatin | | | 1.28 (1.15 to 1.43) | 1.23 (1.13 to 1.33) | NA |
| Chlorzoxazone 500-mg single dose taken 2 hours after rilpivirine | 150 mg once daily[a] | 16 | 0.98 (0.85 to 1.13) | 1.03 (0.95 to 1.13) | NA |
| Darunavir/ritonavir 800/100 mg once daily | 150 mg once daily[a] | 15 | 0.90 (0.81-1.00) | 0.89 (0.81-0.99) | 0.89 (0.68-1.16) |
| Didanosine 400 mg once daily delayed release capsules taken 2 hours before rilpivirine | 150 mg once daily[a] | 13 | 0.96 (0.80-1.14) | 1.12 (0.99-1.27) | NA |
| Digoxin 0.5-mg single dose | 25 mg once daily | 22 | 1.06 (0.97 to 1.17) | 0.98 (0.93 to 1.04)[c] | NA |
| Ethinylestradiol 0.035 mg once daily | 25 mg once daily | 17 | 1.17 (1.06 to 1.30) | 1.14 (1.10 to 1.19) | 1.09 (1.03 to 1.16) |
| Norethindrone 1 mg once daily | | | 0.94 (0.83 to 1.06) | 0.89 (0.84 to 0.94) | 0.99 (0.90 to 1.08) |
| Ketoconazole 400 mg once daily | 150 mg once daily[a] | 14 | 0.85 (0.80 to 0.90) | 0.76 (0.70 to 0.82) | 0.34 (0.25 to 0.46) |
| Lopinavir/ritonavir 400/100 mg twice daily (soft gel capsule) | 150 mg once daily[a] | 15 | 0.96 (0.88-1.05) | 0.99 (0.89-1.10) | 0.89 (0.73-1.08) |
| Methadone 60-100 mg once daily, individualized dose | 25 mg once daily | 13 | | | |
| R(−) methadone | | | 0.86 (0.78 to 0.95) | 0.84 (0.74 to 0.95) | 0.78 (0.67 to 0.91) |
| S(+) methadone | | | 0.87 (0.78 to 0.97) | 0.84 (0.74 to 0.96) | 0.79 (0.67 to 0.92) |
| Metformin 850-mg single dose | 25 mg once daily | 20 | 1.02 (0.95 to -1.10) | 0.97 (0.90 to 1.06)[b] | NA |
| Raltegravir 400 mg twice daily | 25 mg once daily | 23 | 1.10 (0.77-1.58) | 1.09 (0.81-1.47) | 1.27 (1.01-1.60) |
| Rifampin 600 mg once daily | 150 mg once daily[a] | 16 | 1.02 (0.93 to 1.12) | 0.99 (0.92 to 1.07) | NA |
| 25-desacetylrifampin | | | 1.00 (0.87 to 1.15) | 0.91 (0.77 to 1.07) | NA |

TABLE 10-continued

Effect of Rilpivirine on the Pharmacokinetics of Coadministered Drugs

| Coadministered Drug(s) and Dose(s) | Dose of Rilpivirine | n | Geometric Mean Ratio (90% CI) of Coadministered Drug Pharmacokinetic Parameters with/without EDURANT No Effect = 1.00 $C_{max}$ | AUC | $C_{min}$ |
|---|---|---|---|---|---|
| Sildenafil 50-mg single dose | 75 mg once daily[a] | 16 | 0.93 (0.80 to 1.08) | 0.97 (0.87 to 1.08) | NA |
| N-desmethyl-sildenafil | | | 0.90 (0.80 to 1.02) | 0.92 (0.85 to 0.99)[c] | NA |
| Tenofovir disoproxil fumarate 300 mg once daily | 150 mg once daily[a] | 16 | 1.19 (1.06-1.34) | 1.23 (1.16-1.31) | 1.24 (1.10-1.38) |

CI = Confidence Interval;

n = Maximum number of subjects with data;

NA = Not available.

[a]This interaction study has been performed with a dose higher than the recommended dose for rilpivirine (25 mg once daily) assessing the maximal effect on the coadministered drug.

[b]n = (maximum number of subjects with data) for $AUC_{(0-\infty)}$ = 15.

[c]$AUC_{(0-last)}$.

TABLE 11

Effect of Coadministered Drugs on the Pharmacokinetics of Rilpivirine

| Coadministered Drug(s) and Dose(s) | Dose of Rilpivirine | n | Geometric Mean Ratio (90% CI) of Rilpivirine Pharmacokinetic Parameters with/without Coadministered Drugs No Effect = 1.00 $C_{max}$ | AUC | $C_{min}$ |
|---|---|---|---|---|---|
| Acetaminophen 500-mg single dose | 150 mg once daily[a] | 16 | 1.09 (1.01 to 1.18) | 1.16 (1.10 to 1.22) | 1.26 (1.16 to 1.38) |
| Atorvastatin 40 mg once daily | 150 mg once daily[a] | 16 | 0.91 (0.79 to 1.06) | 0.90 (0.81 to 0.99) | 0.90 (0.84 to 0.96) |
| Chlorzoxazone 500-mg single dose taken 2 hours after rilpivirine | 150 mg once daily[a] | 16 | 1.17 (1.08 to 1.27) | 1.25 (1.16 to 1.35) | 1.18 (1.09 to 1.28) |
| Darunavir/ritonavir 800/100 mg once daily | 150 mg once daily[a] | 14 | 1.79 (1.56 to 2.06) | 2.30 (1.98 to 2.67) | 2.78 (2.39 to 3.24) |
| Didanosine 400 mg once daily delayed release capsules taken 2 hours before rilpivirine | 150 mg once daily[a] | 21 | 1.00 (0.90 to 1.10) | 1.00 (0.95 to 1.06) | 1.00 (0.92 to 1.09) |
| Ethinylestradiol/ Norethindrone 0.035 mg once daily/ 1 mg once daily | 25 mg once daily | 15 | ↔[b] | ↔[b] | ↔[b] |
| Ketoconazole 400 mg once daily | 150 mg once daily[b] | 15 | 1.30 (1.13 to 1.48) | 1.49 (1.31 to 1.70) | 1.76 (1.57 to 1.97) |
| Lopinavir/ritonavir 400/100 mg twice daily (soft gel capsule) | 150 mg once daily[a] | 15 | 0.96 (0.88 to 1.05) | 0.99 (0.89 to 1.10) | 0.89 (0.73 to 1.08) |
| Methadone 60-100 mg once daily, individualized dose | 25 mg once daily | 12 | ↔[b] | ↔[b] | ↔[b] |
| Raltegravir 400 mg twice daily | 25 mg once daily | 23 | 1.12 (1.04 to 1.20) | 1.12 (1.05 to 1.19) | 1.03 (0.96 to 1.12) |
| Rifabutin 300 mg once daily | 25 mg once daily | 18 | 0.69 (0.62 to 0.76) | 0.58 (0.52 to 0.65) | 0.52 (0.46 to 0.59) |
| Rifabutin 300 mg once daily | 50 mg once daily | 18 | 1.43 (1.30 to 1.56) | 1.16 (1.06 to 1.26) | 0.93 (0.85 to 1.01) |
| | | | (reference arm for comparison was 25-mg-once-daily rilpivirine administered alone) | | |
| Rifampin 600 mg once daily | 150 mg once daily[a] | 16 | 0.31 (0.27 to 0.36) | 0.20 (0.18 to 0.23) | 0.11 (0.10 to 0.13) |
| Sildenafil 50-mg single dose | 75 mg once daily[a] | 16 | 0.92 (0.85 to 0.99) | 0.98 (0.92 to 1.05) | 1.04 (0.98 to 1.09) |

TABLE 11-continued

| Effect of Coadministered Drugs on the Pharmacokinetics of Rilpivirine | | | | | |
|---|---|---|---|---|---|
| Coadministered Drug(s) and Dose(s) | Dose of Rilpivirine | n | Geometric Mean Ratio (90% CI) of Rilpivirine Pharmacokinetic Parameters with/without Coadministered Drugs No Effect = 1.00 | | |
| | | | $C_{max}$ | AUC | $C_{min}$ |
| Tenofovir disoproxil fumarate 300 mg once daily | 150 mg once daily[a] | 16 | 0.96 (0.81 to 1.13) | 1.01 (0.87 to 1.18) | 0.99 (0.83 to 1.16) |

CI = Confidence Interval;
n = Maximum number of subjects with data;
NA = Not available;
↔ = No change.
[a]This interaction study has been performed with a dose higher than the recommended dose for rilpivirine (25 mg once daily) assessing the maximal effect on the coadministered drug.
[b]Comparison based on historic controls.

Cabotegravir inhibits HIV integrase by binding to the integrase active site and blocking the strand transfer step of retroviral deoxyribonucleic acid (DNA) integration which is essential for the HIV replication cycle. The mean 50% inhibitory concentration ($IC_{50}$) value of cabotegravir in a strand transfer assay using purified recombinant HIV-1 integrase was 3.0 nM.

Rilpivirine is a diarylpyrimidine NNRTI of HIV-1 and inhibits HIV-1 replication by non-competitive inhibition of HIV-1 reverse transcriptase (RT). Rilpivirine does not inhibit the human cellular DNA polymerases α, β, and γ.

Cabotegravir exhibited antiviral activity against laboratory strains of HIV-1 (subtype B, n=4) with mean 50 percent effective concentration ($EC_{50}$) values of 0.22 nM to 1.7 nM in peripheral blood mononuclear cells (PBMCs) and 293 cells. Cabotegravir demonstrated antiviral activity in PBMCs against a panel of 24 HIV-1 clinical isolates (3 in each of group M subtypes A, B, C, D, E, F, and G and 3 in group O) with a median $EC_{50}$ value of 0.19 nM (range: 0.02 nM to 1.06 nM). The median $EC_{50}$ value against subtype B clinical isolates was 0.05 nM (range: 0.02 to 0.50 nM, n=3). Against clinical HIV-2 isolates, the median $EC_{50}$ value was 0.12 nM (range: 0.10 nM to 0.14 nM, n=4).

Rilpivirine exhibited activity against laboratory strains of wild-type HIV-1 in an acutely infected T-cell line with a median $EC_{50}$ value for HIV-1111B of 0.73 nM (0.27 ng/mL). Rilpivirine demonstrated antiviral activity against a broad panel of HIV-1 group M (subtypes A, B, C, D, F, G, and H) primary isolates with $EC_{50}$ values ranging from 0.07 nM to 1.01 nM (0.03 to 0.37 ng/mL) and was less active against group O primary isolates with $EC_{50}$ values ranging from 2.88 to 8.45 nM (1.06 to 3.10 ng/mL).

In cell culture, cabotegravir was not antagonistic in combination with the NNRTI rilpivirine, or the NRTIs emtricitabine (FTC), lamivudine (3TC), or tenofovir disoproxil fumarate (TDF).

The antiviral activity of rilpivirine was not antagonistic when combined with the NNRTIs efavirenz, etravirine, or nevirapine; the NRTIs abacavir, didanosine, emtricitabine, lamivudine, stavudine, tenofovir, or zidovudine; the protease inhibitors amprenavir, atazanavir, darunavir, indinavir, lopinavir, nelfinavir, ritonavir, saquinavir, or tipranavir; the fusion inhibitor enfuvirtide; the CCR5 co-receptor antagonist maraviroc, or the INSTI raltegravir.

Cell Culture: Cabotegravir-resistant viruses were selected during passage of HIV-1 strain IIIB in MT-2 cells in the presence of cabotegravir. Amino acid substitutions in integrase which emerged and conferred decreased susceptibility to cabotegravir included Q146L (fold change: 1.3 to 4.6), S153Y (fold change: 2.8 to 8.4), S153Y (fold change: 6.3 to 6.4), and 1162M (fold change: 2.8). The integrase (IN) substitution T124A also emerged alone (fold change: 1.1 to 7.4 in cabotegravir susceptibility), in combination with S153Y (fold change: 3.6 to 6.6 in cabotegravir susceptibility), or 1162M (2.8-fold change in cabotegravir susceptibility). Cell culture passage of virus harboring integrase substitutions Q148H, Q148K, or Q148R selected for additional substitutions (C56S, V72I, L74M, V75A, T122N, E138K, G140S, G149A, and M1541), with substituted viruses having reduced susceptibility to cabotegravir of 2.0- to 410-fold change. The combinations of E138K+Q148K and V72I+E138K+Q148K conferred the greatest reductions of 53- to 260-fold and 410-fold change, respectively.

Rilpivirine-resistant strains were selected in cell culture starting from wild-type HIV-1 of different origins and subtypes as well as NNRTI-resistant HIV-1. The frequently observed amino acid substitutions that emerged and conferred decreased phenotypic susceptibility to rilpivirine included L100I; K101E; V1061 and A; V1081; E138K and G, Q, R; V179F and I; Y181C and I; V1891; G190E; H221Y; F227C; and M2301 and L.

Clinical Trials: In the pooled Phase 3 FLAIR and ATLAS trials, there were 7 confirmed virologic failures (2 consecutive HIV-1 RNA >200 copies/mL) on cabotegravir plus rilpivirine (7/591, 1.2%) and 7 confirmed virologic failures on current antiretroviral regimen (CAR) (7/591, 1.2%). Of the 7 virologic failures in the cabotegravir plus rilpivirine arm, 6 had post-baseline resistance data. All 6 had on-treatment rilpivirine resistance-associated substitutions K101E, E138A, or E138K in reverse transcriptase, and 5 of them showed reduced phenotypic susceptibility to rilpivirine (range: 2.4- to 7.1-fold).

Additionally, 4 of the 6 (67%) cabotegravir plus rilpivirine virologic failures with post-baseline resistance data had on-treatment INSTI resistance-associated substitutions and reduced phenotypic susceptibility to cabotegravir (Q148R [n=2; 5-fold and 9-fold decreased susceptibility to cabotegravir], G140R [n=1; 7-fold decreased susceptibility to cabotegravir], or N155H [n=1; 3-fold decreased susceptibility to cabotegravir]).

In comparison, 2 of the 7 (29%) virologic failures in the CAR arm who had post-baseline resistance data had on-treatment resistance substitutions and phenotypic resistance to their antiretroviral drugs; both had on-treatment NRTI substitutions, M184V or I, which conferred resistance to emtricitabine or lamivudine in their regimen and 1 of them also had the on-treatment NNRTI resistance substitution G190S, conferring resistance to efavirenz in their regimen.

In Phase 2 clinical trial LATTE-2, virologic failures on cabotegravir plus rilpivirine also showed emergent genotypic and phenotypic cabotegravir and rilpivirine resistance (with emergent INSTI resistance-associated substitution Q148R and NNRTI resistance-associated substitutions K103N, E138G, and K238T).

In Phase 2 clinical trial LATTE, virologic failures on oral cabotegravir plus rilpivirine also showed emergent genotypic and phenotypic cabotegravir and NNRTI resistance (with emergent INSTI resistance-associated substitutions Q148R, E138K+Q148R, E138K+G140A+Q148R, and G140S+Q148R, and rilpivirine resistance-associated substitutions E138Q, K101K/E+E138E/A, K101K/E+E138E/K, K101E+M230L, and K101E.

Five of the 7 cabotegravir plus rilpivirine virologic failures in FLAIR and ATLAS had HIV-1 subtype A1 and had the integrase L74I substitution (IN L74I) detected at baseline and failure timepoints. Subjects with subtype A1 infection whose virus did not have IN L74I at baseline did not experience virologic failure (FLAIR results shown in Table 12). In addition, there was no detectable phenotypic resistance to cabotegravir conferred by the presence of IN L74I at baseline.

The other 2 virologic failures had subtype AG and did not have the IN L74I substitution. Six of the virologic failures with subtype A1 and AG were from Russia where the prevalence of subtypes A, A1, and AG are high. Subtypes A, A1, and AG are uncommon in the United States.

The presence of the IN L74I substitution in other subtypes, such as subtype B commonly seen in the United States, was not associated with virologic failure (Table 12). In contrast to the Phase 3 trials where all virologic failures were subtype A1 or AG, in Phase 2 clinical trials, subtypes of the cabotegravir plus rilpivirine virologic failures included A1, A, B, and C.

TABLE 12

Rate of Virologic Failure in FLAIR Trial: Baseline Analysis (Subtypes A1 and B, and Presence of IN L74I)

| Virologic Failure Rate | Cabotegravir plus Rilpivirine[a] | Current Antiretroviral Regimen[b] |
|---|---|---|
| Subtype A1 | 3/8 (38%) | 1/4 (25%) |
| +IN L74I | 3/5 (60%) | 1/3 (33%) |
| −IN L74I | 0/3 | 0/1 |
| Subtype B | 0/174 | 2/174 (1.2%) |
| +IN L74I | 0/12 | 0/11 |
| −IN L74I | 0/153 | 2/150 (41.3%) |
| Missing | 0/9 | 0/13 |
| Russian | 4/54 (7.4%) | 1/39 (2.6%) |
| +IN L74I | 3/35 (9%) | 1/29 (43.4%) |
| −IN L74I | 1/12 (8.3%) | 0/7 |
| Missing | 0/7 | 0/3 |

[a]There were 4 virologic failures in the cabotegravir arm. One virologic failure in the cabotegravir arm had subtype AG.
[b]There were 3 virologic failures in the CAR arm. Two virologic failures in the cabotegravir arm had subtype B.

Cabotegravir: Cross-resistance has been observed among INSTIs. Cabotegravir had reduced susceptibility (>5-fold change) to recombinant HIV-1 strain NL432 viruses harboring the following integrase amino acid substitutions: G118R, Q148K, Q148R, T66K+L74M, E92Q+N155H, E138A+Q148R, E138K+Q148K/R, G140C+Q148R, G140S+Q148H/K/R, and Q148R+N155H (range: 5.1- to 81-fold). The substitutions E138K+Q148K and Q148R+N155H conferred the greatest reductions in susceptibility of 81- and 61-fold, respectively.

Cabotegravir was active against viruses harboring the NNRTI substitutions K103N or Y188L, or the NRTI substitutions M184V, D67N/K70R/T215Y, or V751/F77L/F116Y/Q151M.

Rilpivirine: Cross-resistance has been observed among NNRTIs. The single NNRTI substitutions K101P, Y181I, and Y181V conferred 52-, 15-, and 12-times fold change to rilpivirine, respectively. The K103N substitution did not show reduced susceptibility to rilpivirine by itself. Combinations of 2 or 3 NNRTI resistance-associated substitutions gave 3.7- to 554-fold change to rilpivirine in 38% and 66% of substitutions, respectively. Considering all available cell culture and clinical data, any of the following amino acid substitutions, when present at baseline, are likely to decrease the antiviral activity of rilpivirine: K101E and P; E138A, G, K, R, and Q; V179L; Y181C, I, and V; Y188L; H221Y; F227C; M2301 and L, and the combination of L100I/K103N.

According to another aspect of the main embodiment, carcinogenesis, mutagenesis, impairment of fertility were reviewed.

Cabotegravir was not carcinogenic in long-term studies in the mouse and rat. Rilpivirine was not carcinogenic in rats. In mice, rilpivirine was positive for hepatocellular neoplasms in both males and females. The observed hepatocellular findings in mice may be rodent specific. At the lowest tested doses in mice, the systemic exposures (based on AUC) to rilpivirine were >17 times the exposure in humans at the MRHD of 25 mg once daily in HIV-1-infected patients or 600-mg IM injection dose of rilpivirine extended-release injectable suspension.

Cabotegravir was not genotoxic in the bacterial reverse mutation assay, mouse lymphoma assay, or in the in vivo rodent micronucleus assay.

Rilpivirine was not genotoxic in the bacterial reverse mutation assay, mouse lymphoma assay, or in the in vivo rodent micronucleus assay.

No human data on the effect of cabotegravir on fertility are available. Cabotegravir when administered orally to male and female rats at 1,000 mg/kg/day (exposure [AUC] >30 times MRHD of 30 mg/day dosed orally or 400-mg intramuscular injection dose) for up to 26 weeks did not cause adverse effects on male or female reproductive organs or spermatogenesis. No functional effects on mating or fertility were observed in male or female rats when administered cabotegravir at doses up to 1,000 mg/kg/day.

No human data on the effect of rilpivirine on fertility are available. In a study conducted in rats, there were no effects on mating or fertility with rilpivirine up to 400 mg/kg/day, a dose of rilpivirine that showed maternal toxicity. This dose is associated with an exposure that is >28 times the exposure in humans at the MRHD of 25 mg once daily or 600-mg intramuscular injection dose of rilpivirine extended-release injectable suspension.

The efficacy of the Combination has been evaluated in two Phase 3 randomized, multicenter, active-controlled, parallel-arm, open-label, non-inferiority trials: Trial 201584 (FLAIR, [NCT02938520]), (n=629): HIV-1-infected, antiretroviral treatment (ART)-naive subjects received a dolutegravir INSTI-containing regimen for 20 weeks (either dolutegravir/abacavir/lamivudine or dolutegravir plus 2 other NRTIs if subjects were HLA-B*5701 positive). Subjects who were virologically suppressed (HIV-1 RNA <50 copies/mL, n=566) were then randomized (1:1) to receive either a cabotegravir plus rilpivirine regimen or remain on the current antiretroviral regimen. Subjects randomized to receive cabotegravir plus rilpivirine initiated treatment with daily oral lead-in dosing with one 30-mg cabotegravir tablet plus one 25-mg rilpivirine tablet for at least 4 weeks followed by treatment with cabotegravir extended-release injectable suspension plus rilpivirine extended-release injectable suspension for an additional 44 weeks.

Trial 201585 (ATLAS, [NCT02951052]), (n=616): HIV-1-infected, ART-experienced, virologically-suppressed (for at least 6 months; median prior treatment duration was 4.3 years) subjects (HIV-1 RNA <50 copies/mL) were randomized and received either a cabotegravir plus rilpivirine regimen or remain on their current antiretroviral regimen. Subjects randomized to receive cabotegravir plus rilpivirine initiated treatment with daily oral lead-in dosing with one 30-mg cabotegravir tablet plus one 25-mg rilpivirine tablet for at least 4 weeks followed by treatment with cabotegravir extended-release injectable suspension plus rilpivirine extended-release injectable suspension for an additional 44 weeks.

The primary analysis was conducted after all subjects completed their Week 48 visit or discontinued the trial prematurely.

At baseline in the pooled analysis, in subjects randomized to receive the Combination, the median age was 38 years, 27% were female, 27% were non-white, and 7% had CD4+ cell count <350 cells/mm$^3$; these characteristics were similar between treatment arms. In ATLAS, subjects received an NNRTI (50%), integrase inhibitor (33%), or protease inhibitor (17%) as their baseline third-agent class prior to randomization; this was similar between treatment arms.

The primary endpoint of FLAIR and ATLAS was the proportion of subjects with plasma HIV-1 RNA ≥50 copies/mL at Week 48 (snapshot algorithm for the Intent-to-Treat-Efficacy [ITT-E] population).

In a pooled analysis of FLAIR and ATLAS, the Combination was non-inferior to current antiretroviral regimen on the proportion of subjects having plasma HIV-1 RNA ≥50 copies/mL (1.9% and 1.7%, respectively) at Week 48. The adjusted treatment difference between the Combination and current antiretroviral regimen (0.2; 95% CI: −1.4, 1.7) for the pooled analysis met the non-inferiority criterion (upper bound of the 95% CI: below 4%). Furthermore, in the pooled analysis, the Combination was non-inferior to current antiretroviral regimen on the proportion of subjects having plasma HIV-1 RNA <50 copies/mL (93.1% and 94.4%, respectively) at Week 48. The adjusted treatment difference between cabotegravir plus rilpivirine and current antiretroviral regimen (−1.4; 95% CI: −4.1, 1.4) for the pooled analysis met the non-inferiority criteria (lower bound of the 95% CI: above −10%).

The non-inferiority result established in FLAIR and ATLAS demonstrated that the length of HIV-1 RNA virologic suppression prior to initiation of the Combination (i.e., <6 months or ≥6 months) did not impact overall response rates.

The primary endpoint and other Week 48 outcomes, including outcomes by key baseline factors, for FLAIR and ATLAS are shown in Tables 13 and 14.

TABLE 13

Virologic Outcomes of Randomized Treatment in FLAIR and ATLAS Trials at Week 48 (Snapshot Algorithm)

| | FLAIR | | ATLAS | |
|---|---|---|---|---|
| Virologic Outcomes | CAB plus RPV (n = 283) | CAR (n = 283) | CAB plus RPV (n = 308) | CAR (n = 308) |
| HIV-1 RNA ≥50 copies/mL[a] | 2% | 2% | 2% | 1% |
| Treatment Difference | −0.4% (95% CI: −2.8%, 2.1%) | | 0.7% (95% CI: −1.2%, 2.5%) | |
| HIV-1 RNA <50 copies/mL | 94% | 93% | 93% | 95% |
| No virologic data at Week 48 window | 4% | 4% | 6% | 4% |
| Discontinued due to adverse event or death | 3% | <1% | 4% | 2% |
| Discontinued for other reasons | 1% | 4% | 2% | 2% |
| Missing data during window but on study | 0 | 0 | 0 | 0 |

[a]Includes subjects who discontinued for lack of efficacy and discontinued while not suppressed.
[b]Adjusted for randomization stratification factors.
n = Number of subjects in each treatment group,
CI = Confidence interval,
CAB = Cabotegravir,
RPV = Rilpivirine,
CAR = Current antiretroviral regimen.

TABLE 14

Proportion of Subjects in FLAIR and ATLAS Trials with Plasma HIV-1 RNA ≥ 50 copies/mL at Week 48 for Key Baseline Factors (Snapshot Algorithm).

| | FLAIR | | ATLAS | |
|---|---|---|---|---|
| Baseline Factors | CAB plus RPV (N = 283) n/N (%) | CAR (N = 283) n/N (%) | CAB plus RPV (N = 308) n/N (%) | CAR (N = 308) n/N (%) |
| Baseline CD4+ (cells/mm3) | | | | |
| <350 | 0/19 | 1/27 (3.7%) | 0/23 | 1/27 (3.7%) |
| ≥350 to <500 | 3/64 (4.7%) | 0/60 | 2/56 (3.6%) | 0/60 |
| ≥500 | 3/200 (1.5%) | 6/196 (3.1%) | 3/299 (1.3%) | 2/224 (0.9%) |

TABLE 14-continued

Proportion of Subjects in FLAIR and ATLAS Trials with Plasma HIV-1 RNA ≥ 50 copies/mL at Week 48 for Key Baseline Factors (Snapshot Algorithm).

| | FLAIR | | ATLAS | |
|---|---|---|---|---|
| Baseline Factors | CAB plus RPV (N = 283) n/N (%) | CAR (N = 283) n/N (%) | CAB plus RPV (N = 308) n/N (%) | CAR (N = 308) n/N (%) |
| Gender | | | | |
| Male | 3/220 (1.4%) | 6/219 (2.7%) | 3/209 (1.4%) | 3/204 (1.5%) |
| Female | 3/63 (4.8%) | 1/64 (1.6%) | 2/99 (2.0%) | 0/104 |
| Race | | | | |
| White | 6/216 (2.8%) | 5/201 (2.5%) | 3/214 (1.4%) | 2/207 (1.0%) |
| African American/African Heritage | 0/47 | 2/56 (3.6%) | 2/62 (3.2%) | 1/77 (1.3%) |
| Asian/Other | 0/20 | 0/24 | 0/32 | 0/24 |
| BMI | | | | |
| <30 kg/m$^2$ | 3/243 (1.2%) | 7/246 (2.8%) | 3/248 (1.2%) | 1/242 (0.4%) |
| ≥30 kg/m$^2$ | 3/40 (7.5%) | 0/37 | 2/60 (3.3%) | 2/66 (3.0%) |
| Age (years) | | | | |
| <50 | 5/250 (2.0%) | 6/254 (2.4%) | 4/242 (1.7%) | 2/212 (0.9%) |
| ≥50 | 1/33 (3.0%) | 1/29 (3.4%) | 1/66 (1.5%) | 1/96 (1.0%) |
| Baseline antiviral therapy at randomization | | | | |
| Protease inhibitor-containing regimen | 0 | 0 | 1/51 (2.0%) | 0/54 |
| Integrase inhibitor-containing regimen | 6/283 (2.1%) | 7/283 (2.5%) | 0/102 | 2/99 (2.0%) |
| Non-nucleoside reverse transcriptase inhibitor-containing regimen | 0 | 0 | 4/155 (2.6%) | 1/55 (0.6%) |

In both the FLAIR and ATLAS trials, treatment differences across baseline characteristics (CD4+ count, gender, age, race, BMI, and baseline third-agent class) were comparable. Subjects in both the FLAIR and ATLAS trials were virologically-suppressed prior to Day 1 or at study entry, respectively, and no clinically relevant change from baseline in CD4+ cell counts was observed.

According to another aspect of the main embodiment, the Combination is supplied in 2 dosing kits containing cabotegravir extended-release injectable suspension 200 mg/mL and rilpivirine extended-release injectable suspension 300 mg/mL, co-packaged as follows:

2-mL (NDC 49702-253-15) Containing:

One 2-mL single-dose vial of cabotegravir extended-release injectable suspension containing 400 mg of cabotegravir.

One 2-mL single-dose vial of rilpivirine extended-release injectable suspension containing 600 mg of rilpivirine 3-mL (NDC 49702-240-15) Containing:

One 3-mL single-dose vial of cabotegravir extended-release injectable suspension containing 600 mg of cabotegravir.

One 3-mL single-dose vial of rilpivirine extended-release injectable suspension containing 900 mg of rilpivirine.

Each 2-mL and 3-mL dosing kit also contains 2 syringes, 2 vial adapters, and 2 needles for intramuscular injection (23-gauge, 1½ inch). The vial stoppers are not made with natural rubber latex.

In an embodiment, the 2-mL single-dose vial of cabotegravir extended-release injectable suspension containing 400 mg of cabotegravir, the 2-mL single-dose vial of rilpivirine extended-release injectable suspension containing 600 mg of rilpivirine, the 3-mL single-dose vial of cabotegravir extended-release injectable suspension containing 600 mg of cabotegravir, and the 3-mL single-dose vial of rilpivirine extended-release injectable suspension containing 900 mg of rilpivirine are packed separately. In an embodiment, each of the 2-mL and 3-mL packages also contain a syringe, a vial adapter and a needle for intramuscular injection (23-gauge, 1½ inch). The vial stoppers are not made with natural rubber latex.

According to another aspect of the main embodiment, the Combination is stored in the refrigerator at 2° to 8° C. (36° to 46° F.) in the original carton until ready to use. Preferably, neither the Combination, nor either component of the Combination is frozen. Preferably, neither the Combination nor any component of the Combination is mixed with any other product or diluent.

Prior to administration, vials should be brought to room temperature (not to exceed 25° C. [77° F.]). Vials may remain in the carton at room temperature for up to 6 hours. If not used after 6 hours, they must be discarded.

Once the suspension has been drawn into the respective syringes, the injections should be administered as soon as possible, but may remain in the syringe for up to 2 hours. If 2 hours are exceeded, the medications, syringes, and needles must be discarded.

As used throughout, one of skill in the art recognizes that the terms "monthly" or similar are interchangeable with "every 4 weeks" or "Q4W". Similarly, terms referring to every 2 months are equivalent for purposes of administration with every 8 weeks or "Q8W". For purposes herein, any month versus 4 week period (or multiple thereof) shall be taken as alternative embodiments.

Second Main Embodiment

According to a second main embodiment, there is provided a method of treating HIV-1, comprising regularly administering intramuscular injections of cabotegravir or a salt thereof and rilpivirine or a salt thereof, subsequent to at least one said intramuscular injection of each of cabotegravir or a salt thereof and rilpivirine or a salt thereof, discontinuing one or both of said regularly administered intramuscular injections, and replacing the one or more discontinued intramuscular injection with regularly administered oral therapy.

The method of treating HIV comprises the use of cabotegravir and/or rilpivirine oral therapy administered subsequent to at least one cabotegravir and/or rilpivirine injection. According to an embodiment, cabotegravir oral therapy is administered subsequent to at least one cabotegravir injection. Alternatively, rilpivirine oral therapy is administered subsequent to at least one rilpivirine injection.

According to the embodiment, if a patient plans to miss a scheduled injection visit, oral therapy is used in place of one or more injections after initiation of the injection schedule. Injection dosing may be resumed on schedule after oral dosing, in which case the oral dose performs the function of a bridging dose between injections. In an embodiment, in case more than 2 months need to be covered for, i.e. missing more than 2 monthly injections, an alternative oral regimen should be initiated one month or 2 months (±7 days) after the final intramuscular injection. In an embodiment, in case more than 2 months need to be covered for, i.e. missing more than one every 2 months injection, an alternative oral regimen should be initiated 2 months (±7 days) after the final intramuscular injection.

By way of example, if a patient plans to miss a scheduled injection visit by more than 7 days, oral therapy (e.g. one 30-mg tablet of cabotegravir and one 25-mg tablet of rilpivirine once daily) may be used to replace injections. Preferably, the oral therapy replaces 2 or fewer injections. The first dose of oral therapy should be taken approximately when the missed injection would have been administered, e.g. 1 month after the last injection dose in the case of monthly administration schedules. Injection dosing should be resumed on the day oral dosing completes (see Table 2 above). The first dose of oral therapy should be taken approximately when the missed injection would have been administered, e.g. 2 months (±7 days) after the last injection dose in the case of two monthly administration schedules. Injection dosing should be resumed on the day oral dosing completes.

By way of example, if a patient, who is on monthly injection dosing of Rilpivirine long acting, misses injections or oral therapy or is on oral bridging therapy by <2 months, the patient should continue with the monthly 600 mg (2 mL) injection dosing schedule as soon as possible. By way of example, if a patient, who is on monthly injection dosing of Rilpivirine long acting, misses injections or oral therapy or is on oral bridging therapy by ≥2 months, the patient should re-initiate the patient on the 900 mg (3 mL) dose, and then continue to follow the monthly 600 mg (2 mL) injection dosing schedule. (Table 15)

By way of example, if a patient, who is on 2 monthly injection dosing of Rilpivirine long acting, misses a scheduled injection visit or oral therapy or is on oral bridging therapy by ≤2 months, the patient should resume with 3 mL (900 mg) injections of rilpivirine long acting formulation as soon as possible and continue with the every 2 months injection dosing schedule. In an embodiment, the patient missed injection 2 (month 3). By way of example, if a patient, who is on 2 monthly injection dosing of Rilpivirine long acting, misses a scheduled injection visit or oral therapy or is on oral bridging therapy by >2 months, the patient should re-initiate treatment with a 3 mL (900 mg) injection of rilpivirine long acting formulation, followed by a second 3 mL (900 mg) initiation injection of rilpivirine long acting formulation one month later. Then follow the every 2 months injection dosing schedule. In an embodiment, the patient missed injection 2 (month 3). (Table 16)

By way of example, if a patient, who is on 2 monthly injection dosing of Rilpivirine long acting, misses a scheduled injection visit or oral therapy or is on oral bridging therapy by ≤3 months, the patient should resume with 3 mL (900 mg) injections of rilpivirine long acting formulation as soon as possible and continue with the every 2 month injection dosing schedule. In an embodiment, the patient missed injection 3 or later (month 5 onwards). By way of example, if a patient, who is on 2 monthly injection dosing of Rilpivirine long acting, misses a scheduled injection visit or oral therapy or is on oral bridging therapy by >3 months, the patient should re-initiate treatment on the 3 mL (900 mg) injections of rilpivirine long acting formulation, followed by a second 3 mL (900 mg) initiation injection of rilpivirine long acting formulation one month later. Then follow the every 2 month injection dosing schedule. In an embodiment, the patient missed injection 3 or later (month 5 onwards). (Table 16).

TABLE 15

Rilpivirine long-acting dosing recommendations after missed injections or oral therapy or on oral bridging therapy for patients on monthly injection dosing

| Time since last injection | Recommendation |
|---|---|
| ≤2 months: | Continue with the monthly 600 mg (2 mL) injection dosing schedule as soon as possible. |
| >2 months: | Re-initiate the patient on the 900 mg (3 mL) dose, and then continue to follow the monthly 600 mg (2 mL) injection dosing schedule. |

TABLE 16

Rilpivirine long-acting dosing recommendations after missed injections or oral therapy or on oral bridging therapy for patients on every 2 months injection dosing

| Missed Injection Visit | Time since last injection | Recommendation (all injections are 3 mL) |
|---|---|---|
| Injection 2 (month 3) | ≤2 months | Continue with the 900 mg (3 mL) injection as soon as possible and continue with every 2 months injection dosing schedule. |
| | >2 months | Re-initiate the patient on the 900 mg (3 mL) dose, followed by a second 900 mg (3 mL) initiation injection one month later. Then follow the every 2 months injection dosing schedule. |
| Injection 3 or later (month 5 onwards) | ≤3 months | Continue with the 900 mg (3 mL) injection as soon as possible and continue with every 2 months injection dosing schedule. |
| | >3 months | Re-initiate the patient on the 900 mg (3 mL) dose, followed by a second 900 mg (3 mL) initiation injection one month later. Then follow the every 2 months injection dosing schedule. |

Third Main Embodiment

According to a third main embodiment, a method of treating HIV is provided, comprising regularly administering intramuscular injections of cabotegravir or a salt thereof and rilpivirine or a salt thereof, subsequent to at least one said intramuscular injection of each of cabotegravir or a salt thereof and rilpivirine or a salt thereof, discontinuing one or both of said regularly administered intramuscular injections, and reestablishing intramuscular administration of the one or both cabotegravir or a salt thereof and rilpivirine or a salt thereof, by first administering a loading dose of the discontinued cabotegravir or a salt thereof and/or rilpivirine or a salt thereof, and then continuing the regular administration of the intramuscular injections.

According to this embodiment, a re-initiation injection of the Combination is given after at least one prior injection and after delay of a subsequently scheduled injection outside of an allowable treatment window, wherein the re-initiation injection is a higher dose than the scheduled injection.

According to one embodiment, re-initiation uses the 3-mL dose of cabotegravir, and then continue to follow a monthly 2-mL injection dosing schedule for cabotegravir. According to one embodiment, re-initiation uses the 3-mL dose of rilpivirine, and then continue to follow a monthly 2-mL injection dosing schedule for rilpivirine. According to one embodiment, re-initiation uses the 3-mL dose of the Combination, and then continue to follow a monthly 2-mL injection dosing schedule for the Combination.

Fourth Main Embodiment

According to a fourth main embodiment, a method of treating HIV is provided, comprising regularly administering intramuscular injections of cabotegravir or a salt thereof and rilpivirine or a salt thereof, subsequent to viral suppression by a bictegravir-containing regimen. Alternatively, according to an aspect of this embodiment, there is provided cabotegravir or a salt thereof and rilpivirine or a salt thereof for use in therapy, in particular in the treatment of HIV infection, comprising regularly administering intramuscular injections of cabotegravir or a salt thereof and rilpivirine or a salt thereof, subsequent to viral suppression by a bictegravir-containing regimen.

According to this embodiment, the bictegravir-containing regimen is a bictegravir/emtricitabine/tenofovir alafenamide single tablet regimen. Further according to this embodiment, the bictegravir is administered 50 mg/day.

According to this embodiment, the regularly administered intramuscular injections are administered approximately every 4 weeks, or alternatively, administered every month. According to another embodiment, the regularly administered intramuscular injections are administered approximately every 8 weeks, or alternatively, administered every two months.

According to this embodiment, the method of regularly administering intramuscular injections of cabotegravir or a salt thereof and rilpivirine or a salt thereof is clinically non-inferior to a treatment with the bictegravir-containing regimen. According to a further embodiment, the method of regularly administering intramuscular injections of cabotegravir or a salt thereof and rilpivirine or a salt thereof is clinically non-inferior over a period of at least 12 months.

Example 1

ATLAS (NCT02951052) and FLAIR (NCT02938520) are two randomized, open-label, international phase 3 studies that demonstrated non-inferiority of switching to monthly intramuscular (IM) injections of CAB LA+RPV LA vs. current antiretroviral regimen (CAR). The injectable CAB+RPV LA regimen requires monthly injection visits within a pre-specified time window, representing a paradigm-shift for patients from daily oral dosing.

Injections were scheduled Q4 weeks with a ±7-day dosing window of the projected dosing date. Adherence to LA therapy was calculated as the number of on-time injection visits occurring within the dosing window, divided by the number of expected dosing visits through Week 48. Oral bridging (the use of oral dosing to cover planned missed injections) was permitted in both trial protocols to enable dosing flexibility for planned absences from a clinical site (e.g. for vacation or travel), while allowing subjects to remain on LA dosing in the long term. Injection visits outside the pre-specified window and missed injection visits with/without use of oral dosing were quantified.

From amongst the ATLAS and FLAIR clinical trials, oral dosing (CAB 30 mg+RPV 25 mg) between in injections was used in 15 subjects in the 48 Week study period.

6 subjects used oral bridging but did not miss a planned injection visit.

2 subjects were unable to continue on LA therapy.

9 missed injections occurred across both studies, with 8 covered by oral bridging (7 subjects).

1 subject had a missed injection visit without coverage by planned oral bridging at Week 32 (stopping criteria met due to acute hepatitis A); however, LA therapy was continued at Week 36 and viral suppression was maintained.

TABLE 17

Summary of 7 subjects having missed injections bridged by oral tablet.

| Patient # | ATLAS/ FLAIR | Injection visit (s) covered by oral bridging (Week) | Duration of oral bridging (days) | Viral load at restart (copies/mL) | Viral load at 48 Weeks (copies/mL) |
|---|---|---|---|---|---|
| 1 | FLAIR | 16 and 20 | 53 | <50 | <50 |
| 2 | FLAIR | 48 | 29 | <50 | <50 |
| 3 | FLAIR | 48 | 20 | <50 | <50 |
| 4 | ATLAS | 32 | 28 | <50 | <50 |
| 5 | ATLAS | 32 | 28 | <50 | <50 |
| 6 | ATLAS | 24 | 21 | <50 | <50 |
| 7 | ATLAS | 16 | 29 | <50 | <50 |

For subjects with planned missed injection visits, oral bridging was found to be an effective strategy for maintaining virologic suppression; no cases of confirmed virologic failure were observed during a period of oral bridging or following resumption of IM dosing.

Example 2

A two-compartment model with first-order oral and intramuscular (IM) absorption and first-order elimination adequately described the data from 23,926 concentration records in 1647 subjects following oral and LA administration (Han K, Patel P, Baker M, et al. Population pharmacokinetics of cabotegravir in adult healthy subjects and HIV-1 infected patients following administration of oral tablet and long acting intramuscular injection. Abstract WEPDB0205. 22nd International AIDS Conference 23-27 Jul. 2018, Amsterdam, the Netherlands).

Covariates retained in the model included gender, BMI, needle length, and split injection on absorption rate constant following LA administration (KA LA) and current smoker status and body weight on CL and volume. No CAB dose adjustment is necessary for the covariates evaluated.

The 5th percentile of the individual predicted concentration (IPRED) of trough following the loading dose in Phase 3 studies from the final model output (0.65 μg/mL) was used as a benchmark to assess the impact of aberrations in dosing against the standard regimen (Orkin C, Arasteh K, Hernindez-Mora M G, et al. Long-acting cabotegravir+rilpivirine for HIV maintenance: FLAIR week 48 results. Conference on Retroviruses and Opportunistic Infections (CROI). Abstract Number: 140. Mar. 4-7, 2019, Seattle, WA.; Swindells S, Andrade-Villanueva J F, Richmond G J, et al. Long-acting cabotegravir+rilpivirine as maintenance therapy: ATLAS week 48 results. Conference on Retroviruses and Opportunistic Infections (CROI). Abstract Number: 139. Mar. 4-7, 2019, Seattle, WA.). The protein-adjusted IC90 (PA-IC90, 0.166 μg/mL) was also considered when assessing the acceptability of a dosing delay.

Long-term safety threshold was assigned of 13.1 μg/mL, the median steady-state Cmax following the highest oral dose of CAB 60 mg QD administered for 96 weeks in Study LAI116482 (LATTE) (Margolis D A, Brinson C C, Smith G H R, et al. LAI116482 Study Team. Cabotegravir plus rilpivirine, once a day, after induction with cabotegravir plus nucleoside reverse transcriptase inhibitors in antiretroviral-naive adults with HIV-1 infection (LATTE): a randomised, phase 2b, dose-ranging trial. Lancet Infect Dis. 2015 October; 15(10):1145-1155).

1- to 12-week delays in dosing of the 2nd, 3rd, and 4th injection were simulated (Table 1). Q4W dosing was resumed after each delay.

A blended population of males (80%) and females (20%) was assumed to represent the expected population. Each scenario included 5000 virtual subjects to ensure 1000 female virtual subjects. Individual PK parameters were calculated by the population parameter estimates, subject-specific NONMEM inter-individual errors (ETAs) sampled from the distributions that are decided by the estimated variance-covariate matrix of between-subject variability and by subject-specific covariates.

Scenarios of Delayed Dosing for CAB Monthly Treatment Regimen (CAB LA 600 mg (3 mL) Initial Injection Followed by 400 mg (2 mL) with RPV LA Q4W) (Table 18)

TABLE 18

| Sim | Late | | Time Relative to 1st LA Dose (Time Zero) in Weeks | | | | | | | | | | | | | | | | | | | |
|---|---|---|---|---|---|---|---|---|---|---|---|---|---|---|---|---|---|---|---|---|---|---|
| # | Dose | WD | 0 | 4 | 5 | 6 | 7 | 8 | 9 | 10 | 11 | 12 | 13 | 14 | 15 | 16 | 17 | 18 | 19 | 20 | 22 | 24 |
| 1 | None | 0 | 3 | 2 | | | | 2 | | | | 2 | | | | 2 | | | | 2 | | |
| 2 | Delay | 1 | 3 | | 2 | | | | 2 | | | | 2 | | | | 2 | | | | | |
| 3 | the | 2 | 3 | | | 2 | | | | 2 | | | | 2 | | | | 2 | | | 2 | |
| 4 | $2^{nd}$ | 3 | 3 | | | | 2 | | | | 2 | | | | 2 | | | | 2 | | | |
| 5 | IM | 4 | 3 | | | | | 2 | | | | 2 | | | | 2 | | | | 2 | | 2 |
| 6 | Dose | 4 | 3 | | | | | 3 | | | | 2 | | | | 2 | | | | 2 | | 2 |
| 7 | | 6 | 3 | | | | | | | 2 | | | | 2 | | | | 2 | | | 2 | |
| 8 | | 8 | 3 | | | | | | | | | 2 | | | | 2 | | | | 2 | | 2 |
| 9 | | 8 | 3 | | | | | | | | | 3 | | | | 2 | | | | 2 | | 2 |

TABLE 18-continued

| Sim # | Late Dose | WD | Time Relative to 1st LA Dose (Time Zero) in Weeks 0 | 4 | 5 | 6 | 7 | 8 | 9 | 10 | 11 | 12 | 13 | 14 | 15 | 16 | 17 | 18 | 19 | 20 | 22 | 24 |
|---|---|---|---|---|---|---|---|---|---|---|---|---|---|---|---|---|---|---|---|---|---|---|
| 10 | | 12 | 3 | | | | | | | | | | | | | 2 | | | | 2 | | 2 |
| 11 | | 12 | 3 | | | | | | | | | | | | | 3 | | | | 2 | | 2 |
| 12 | Delay | 1 | 3 | 2 | | | | | 2 | | | | 2 | | | | 2 | | | | | |
| 13 | the | 2 | 3 | 2 | | | | | | 2 | | | | 2 | | | | 2 | | | 2 | |
| 14 | $3^{rd}$ | 3 | 3 | 2 | | | | | | | 2 | | | | 2 | | | | 2 | | | |
| 15 | IM | 4 | 3 | 2 | | | | | | | | 2 | | | | 2 | | | | 2 | | 2 |
| 16 | Dose | 4 | 3 | 2 | | | | | | | | 3 | | | | 2 | | | | 2 | | 2 |
| 17 | | 6 | 3 | 2 | | | | | | | | | | 2 | | | | 2 | | | 2 | |
| 18 | | 8 | 3 | 2 | | | | | | | | | | | | 2 | | | | 2 | | 2 |
| 19 | | 8 | 3 | 2 | | | | | | | | | | | | 3 | | | | 2 | | 2 |
| 20 | | 12 | 3 | 2 | | | | | | | | | | | | | | | | 2 | | 2 |
| 21 | | 12 | 3 | 2 | | | | | | | | | | | | | | | | 3 | | 2 |
| 22 | Delay | 1 | 3 | 2 | | | | 2 | | | | | 2 | | | | 2 | | | | | |
| 23 | the | 2 | 3 | 2 | | | | 2 | | | | | | 2 | | | | 2 | | | 2 | |
| 24 | $4^{th}$ | 3 | 3 | 2 | | | | 2 | | | | | | | 2 | | | | 2 | | | |
| 25 | IM | 4 | 3 | 2 | | | | 2 | | | | | | | | 2 | | | | 2 | | 2 |
| 26 | Dose | 4 | 3 | 2 | | | | 2 | | | | | | | | 3 | | | | 2 | | 2 |
| 27 | | 6 | 3 | 2 | | | | 2 | | | | | | | | | | 2 | | | 2 | |
| 28 | | 8 | 3 | 2 | | | | 2 | | | | | | | | | | | | 2 | | 2 |
| 29 | | 8 | 3 | 2 | | | | 2 | | | | | | | | | | | | 3 | | 2 |
| 30 | | 12 | 3 | 2 | | | | 2 | | | | | | | | | | | | | | 2 |
| 31 | | 12 | 3 | 2 | | | | 2 | | | | | | | | | | | | | | 3 |

Sim: simulation.
WD: weeks delayed.
3 = 600 mg (3 mL).
2 = 400 mg (2 mL).
Sim #s 6, 9, 11, 16, 19, 21, 26, 29, 31: reinitiation with loading dose after delay.
Not all visits are shown between Week 20 and 24.

Oral bridging started at the time of the missed injection for a duration of 1-2 months when CAB LA dosing was resumed (Table 18). The 4th IM dose was assumed to be missed. Dosing resumed the Q4W pattern.

TABLE 19

| Sim # | OB | Time Relative to $1^{st}$ LA Dose (Time Zero) in Weeks 0 | 4 | 8 | 12 | 13 | 14 | 15 | 16 | 17 | 18 | 19 | 20 |
|---|---|---|---|---|---|---|---|---|---|---|---|---|---|
| 32 | 4 | 3 | 2 | 2 | OB | OB | OB | OB | 2 | | | | 2 |
| 33 | 6 | 3 | 2 | 2 | OB | OB | OB | OB | OB | OB | 2 | | |
| 34 | 8 | 3 | 2 | 2 | OB | OB | OB | OB | OB | OB | OB | OB | 2 |
| 35 | 8 | 3 | 2 | 2 | OB | OB | OB | OB | OB | OB | OB | OB | 3 |

OB: duration of oral bridging in weeks.
Sim: simulation.
3 = 600 mg (3 mL).
2 = 400 mg (2 mL).
OB = oral bridging daily.

The results of the simulations run in accordance with the above are shown in FIG. 1. Simulated Concentration-versus-Time Profiles for a) no delay (Sim #1), b) Injection 2 delayed by 1 week (Sim #2), c) Injection 3 delayed by 4 weeks with 2 mL or 3 mL re-initiation (Sim #15, Sim #16), d) Injection 4 delayed by 4 weeks with 2 mL or 3 mL re-initiation (Sim #25, Sim #26), e) 4-week delay at Injection 4 with and without oral bridge (Sim #25, Sim #32) and f) 8-week delay at Injection 4 with and without oral bridge (Sim #29, Sim #35).

The invention claimed is:

1. A method of treating HIV-1 infection in a subject comprising:

(a) intramuscularly administering to the subject once every month±7 days a dosage regimen comprising a 2-mL injection of 400 mg of cabotegravir and a separate 2-mL injection of 600 mg of rilpivirine (once-monthly dosing);

(b) replacing said once-monthly dosing with oral antiretroviral therapy comprising cabotegravir and rilpivirine, wherein the first dose of said oral antiretroviral therapy is administered 1 month ±7 days after the last administration of said once-monthly dosing;

(c) discontinuing said oral antiretroviral therapy; and (d) wherein if 2 months or less has passed between the last injection of said once-monthly dosing and the last day of said oral antiretroviral therapy, resuming said once-monthly dosing on the last day of said oral antiretroviral therapy; or wherein if greater than 2 months has passed between the last injection of said once-monthly dosing and the last day of said oral antiretroviral therapy, intramuscularly administering to the subject a 3-mL injection of 600 mg of cabotegravir and a separate 3-mL injection of 900 mg of rilpivirine (reinitiation injections) on the last day of said oral antiretroviral therapy and then resuming said once-monthly dosing one month ±7 days after said reinitiation injections.

2. The method of claim 1, further comprising intramuscularly administering to the subject one month±7 days prior to said once-monthly dosing of step (a) a 3-mL injection of 600 mg of cabotegravir and a separate 3-mL injection of 900 mg of rilpivirine (initiation injections).

3. The method of claim 2, wherein the subject exhibits a viral load of less than 50 copies of HIV-1 virus particles per ml of blood plasma (<50c/mL) after at least 48 weeks of said treatment.

4. The method of claim 1, wherein the subject exhibits a viral load of less than 50 copies of HIV-1 virus particles per mL of blood plasma (<50c/ml) prior to said once-monthly dosing of step (a).

5. The method of claim 2, wherein the subject exhibits a viral load of less than 50 copies of HIV-1 virus particles per mL of blood plasma (<50c/ml) prior to said initiation injections.

6. The method of claim 3, wherein the subject exhibits a viral load of less than 50 copies of HIV-1 virus particles per mL of blood plasma (<50c/ml) prior to said initiation injections.

7. The method of claim 1, wherein 2 months or less has passed between the last injection of said once-monthly dosing and the last day of said oral antiretroviral therapy.

8. The method of claim 7, wherein the subject exhibits a viral load of less than 50 copies of HIV-1 virus particles per mL of blood plasma (<50c/ml) after at least 48 weeks of said treatment.

9. The method of claim 8, further comprising intramuscularly administering to the subject one month±7 days prior to said once-monthly dosing of step (a) a 3-mL injection of 600 mg of cabotegravir and a separate 3-mL injection of 900 mg of rilpivirine (initiation injections).

10. The method of claim 9, wherein the subject exhibits a viral load of less than 50 copies of HIV-1 virus particles per mL of blood plasma (<50c/ml) prior to said initiation injections.

11. The method of claim 1, wherein greater than 2 months has passed between the last injection of said once-monthly dosing and the last day of said oral antiretroviral therapy.

12. The method of claim 11, wherein the subject exhibits a viral load of less than 50 copies of HIV-1 virus particles per mL of blood plasma (<50c/ml) after at least 48 weeks of said treatment.

13. The method of claim 12, further comprising intramuscularly administering to the subject one month±7 days prior to said once-monthly dosing of step (a) a 3-mL injection of 600 mg of cabotegravir and a separate 3-mL injection of 900 mg of rilpivirine (initiation injections).

14. The method of claim 13, wherein the subject exhibits a viral load of less than 50 copies of HIV-1 virus particles per mL of blood plasma (<50c/ml) prior to said initiation injections.

15. A method of treating HIV-1 infection in a subject comprising:

(a) intramuscularly administering to the subject a 3-mL injection of 600 mg of cabotegravir and a separate 3-mL injection of 900 mg of rilpivirine (initiation injections);

(b) initiating administration of an oral antiretroviral therapy comprising cabotegravir and rilpivirine to the subject, wherein the first dose of said oral antiretroviral therapy is administered 1 month±7 days after said initiation injections;

(c) discontinuing said oral antiretroviral therapy; and (d) wherein if 2 months or less has passed between said initiation injections and the last day of said oral antiretroviral therapy, intramuscularly administering to the subject once every month±7 days a dosage regimen comprising a 2-mL injection of 400 mg of cabotegravir and a separate 2-mL injection of 600 mg of rilpivirine (once-monthly dosing) starting on the last day of said oral antiretroviral therapy; or wherein if greater than 2 months has passed between said initiation injections and the last day of said oral antiretroviral therapy, intramuscularly administering to the subject a 3-mL injection of 600 mg of cabotegravir and a separate 3-mL injection of 900 mg of rilpivirine (reinitiation injections) on the last day of said oral antiretroviral therapy and then initiating said once-monthly dosing one month±7 days after said reinitiation injections.

16. The method of claim 15, wherein the subject exhibits a viral load of less than 50 copies of HIV-1 virus particles per ml of blood plasma (<50c/mL) after at least 48 weeks of said treatment.

17. The method of claim 15, wherein the subject exhibits a viral load of less than 50 copies of HIV-1 virus particles per mL of blood plasma (<50c/ml) prior to said initiation injections.

18. The method of claim 16, wherein the subject exhibits a viral load of less than 50 copies of HIV-1 virus particles per mL of blood plasma (<50c/ml) prior to said initiation injections.

19. The method of claim 15, wherein 2 months or less has passed between the last injection of said once-monthly dosing and the last day of said oral antiretroviral therapy.

20. The method of claim 19, wherein the subject exhibits a viral load of less than 50 copies of HIV-1 virus particles per mL of blood plasma (<50c/ml) after at least 48 weeks of said treatment.

21. The method of claim 20, wherein the subject exhibits a viral load of less than 50 copies of HIV-1 virus particles per mL of blood plasma (<50c/ml) prior to said initiation injections.

22. The method of claim 15, wherein greater than 2 months has passed between said initiation injections and the last day of said oral antiretroviral therapy.

23. The method of claim 22, wherein the subject exhibits a viral load of less than 50 copies of HIV-1 virus particles per mL of blood plasma (<50c/ml) after at least 48 weeks of said treatment.

24. The method of claim 23, wherein the subject exhibits a viral load of less than 50 copies of HIV-1 virus particles per mL of blood plasma (<50c/ml) prior to said initiation injections.

* * * * *